United States Patent
Sakamoto

(10) Patent No.: US 10,432,916 B2
(45) Date of Patent: Oct. 1, 2019

(54) MEASUREMENT APPARATUS AND OPERATION METHOD OF MEASUREMENT APPARATUS

(71) Applicant: OLYMPUS CORPORATION, Tokyo (JP)

(72) Inventor: Yohei Sakamoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 16/056,592

(22) Filed: Aug. 7, 2018

(65) Prior Publication Data

US 2019/0068956 A1 Feb. 28, 2019

(30) Foreign Application Priority Data

Aug. 31, 2017 (JP) ................................. 2017-167054

(51) Int. Cl.
| | | |
|---|---|---|
| *H04N 13/00* | (2018.01) | |
| *H04N 7/18* | (2006.01) | |
| *H04N 13/296* | (2018.01) | |
| *H04N 13/204* | (2018.01) | |
| *G06T 7/73* | (2017.01) | |

(Continued)

(52) U.S. Cl.
CPC ............. *H04N 13/296* (2018.05); *A61B 1/00* (2013.01); *G06T 7/74* (2017.01); *H04N 13/204* (2018.05); *H04N 13/239* (2018.05); *H04N 13/246* (2018.05); *H04N 13/254* (2018.05); *H04N 13/398* (2018.05); *G06T 2207/10012* (2013.01); *H04N 2013/0081* (2013.01); *H04N 2213/001* (2013.01)

(58) Field of Classification Search
CPC .. H04N 13/296; H04N 13/204; H04N 13/246; H04N 13/293; H04N 13/254; H04N 13/239; H04N 13/398; H04N 2013/0081; H04N 2213/001; H04N 7/18; G06T 7/74; G06T 2207/10012; G01N 21/954; A61B 1/00; A61B 1/07; A61B 1/00193; A61B 1/041
USPC ....... 348/42, 45, 46, 49–51, 54, 68, 65, 135, 348/125; 356/241.1; 385/117; 600/101, 600/111; 382/154
See application file for complete search history.

(56) References Cited

U.S. PATENT DOCUMENTS

| | | | | |
|---|---|---|---|---|
| 2009/0167847 A1* | 7/2009 | Doi | .................... | A61B 1/00096 348/65 |
| 2013/0038606 A1* | 2/2013 | Ushiki | ................. | H04N 13/128 348/46 |
| 2018/0342074 A1* | 11/2018 | Sakamoto | ................. | G06T 7/55 |

FOREIGN PATENT DOCUMENTS

JP 5728399 B2 6/2015

\* cited by examiner

*Primary Examiner* — Sherrie Hsia
(74) *Attorney, Agent, or Firm* — Scully Scott Murphy & Presser, P.C.

(57) ABSTRACT

A reliability determination unit determines a measurement reliability on the basis of a point on a first parallax image. An imaging condition determination unit determines whether imaging conditions of an imaging unit have changed after the reliability determination unit determines that the measurement reliability is low. The imaging unit captures an image of an object which is a measurement target and generates a second parallax image after the reliability determination unit determines that the measurement reliability is low. The reliability determination unit determines the measurement reliability on the basis of a point on the second parallax image after the imaging condition determination unit determines that the imaging conditions have changed.

13 Claims, 21 Drawing Sheets

(51) Int. Cl.
*H04N 13/398* (2018.01)
*A61B 1/00* (2006.01)
*H04N 13/254* (2018.01)
*H04N 13/246* (2018.01)
*H04N 13/239* (2018.01)

MEASUREMENT APPARATUS AND OPERATION METHOD OF MEASUREMENT APPARATUS

BACKGROUND OF THE INVENTION

Field of the Invention

The present invention relates to a measurement apparatus and an operation method of the measurement apparatus.

Priority is claimed on Japanese Patent Application No. 2017-167054, filed on Aug. 31, 2017, the content of which is incorporated herein by reference.

Description of Related Art

Industrial endoscope apparatuses are used for observation and inspection of internal damage, corrosion and the like of boilers, turbines, engines, pipes and the like. In such an endoscope apparatus, a plurality of types of optical adapters for observing and inspecting various structures are prepared. Optical adapters are provided at the tips of endoscopes and are exchangeable. There is a stereo optical adapter in which two optical systems having different parallaxes are incorporated as such optical adaptors. It is possible to realize three-dimensional measurement in endoscope apparatuses by using such a stereo optical adapter. Endoscope apparatuses for three-dimensional measurement have a function of measuring length, area and the like on the basis of designated measurement points in a captured image.

Endoscope apparatuses for three-dimensional measurement are required to measure the lengths and areas of damage and defects of subjects correctly and accurately. However, for correct and accurate measurement, various conditions such as a positional relationship between a subject and an endoscope, brightness of illumination, the shape of the subject, properties of the subject and the like must be appropriately set. A positional relationship between a subject and an endoscope includes an object distance, an imaging angle and the like. It is very difficult for users with a low degree of skill who are unaccustomed to using a measurement function to appropriately set such conditions. To realize a measurement function which is also easily used by users with a low degree of skill, it is important to obtain images suitable for measurement by providing some support from a computer when images used for measurement are obtained.

For example, in Japanese Patent No. 5728399, a plurality of images having different parallaxes are obtained. A designation point is designated by a user in a first image temporarily selected from the plurality of images. In each image, a corresponding point corresponding to the designation point designated in the first image is searched for. An error in an image pair composed of the first image and another image is calculated for each image pair. Further, an error is also calculated for an image pair composed of two images other than the first image in the same manner. Accordingly, it is possible to provide measurement using an image pair having a small error, that is, a high measurement reliability, to the user.

SUMMARY OF THE INVENTION

According to a first aspect of the present invention, a measurement apparatus includes an imaging unit, a display control unit, a designation point setting unit, a point detection unit, a reliability determination unit, a measurement unit, and an imaging condition determination unit. The imaging unit captures an image of an object which is a measurement target and generates a parallax image including two images having a parallax therebetween. The display control unit causes a display unit to display at least one of the two images. The two images displayed on the display unit are included in a first parallax image which is the parallax image generated when an image of the object is captured at a first timing. The designation point setting unit sets a designation point in an image which is one of the two images included in the first parallax image and is displayed on the display unit. The point detection unit detects a corresponding point corresponding to the designation point in an image which is the other of the two images included in the first parallax image and differs from the image in which the designation point has been set. The reliability determination unit determines a measurement reliability on the basis of the designation point and the corresponding point. The measurement unit performs measurement of the object using the parallax image when the reliability determination unit determines that the measurement reliability is high. The imaging condition determination unit determines whether imaging conditions of the imaging unit have changed from imaging conditions at the first timing after the reliability determination unit determines that the measurement reliability is low. After the reliability determination unit determines that the measurement reliability is low, the imaging unit captures an image of the object at a second timing and generates a second parallax image which is the parallax image including the two images. After the imaging condition determination unit determines that the imaging conditions have changed, the point detection unit detects a similar point in one of the two images included in the second parallax image. The similar point is similar to the designation point set in one of the two images included in the first parallax image. The point detection unit detects a similar corresponding point corresponding to the similar point in an image which is the other of the two images included in the second parallax image and differs from the image in which the similar point is detected. The reliability determination unit determines the measurement reliability on the basis of the similar point and the similar corresponding point.

According to a second aspect of the present invention, in the first aspect, the imaging condition determination unit may determine whether the imaging conditions of the imaging unit have changed from the imaging conditions at the first timing after the second parallax image is generated.

According to a third aspect of the present invention, in the first aspect, the imaging unit may capture an image of the object at the second timing and generate the second parallax image after the reliability determination unit determines that the measurement reliability is low and the imaging condition determination unit determines that the imaging conditions have changed.

According to a fourth aspect of the present invention, in the first aspect, the measurement apparatus may further include a notification control unit which notifies a user of information for increasing the measurement reliability after the reliability determination unit determines that the measurement reliability is low and before the second parallax image is acquired.

According to a fifth aspect of the present invention, in the fourth aspect, the notification control unit may notify the user of the information for encouraging the user to change at least one of the position of the imaging unit and the posture of the imaging unit.

According to a sixth aspect of the present invention, in the fifth aspect, the notification control unit may notify the user of the information for encouraging the user to change at least one of the position of the imaging unit and the posture of the imaging unit such that an object distance between an optical system and the object changes. The optical system causes light from the object to enter the imaging unit.

According to a seventh aspect of the present invention, in the sixth aspect, the measurement apparatus may further include an object distance measurement unit which measures the object distance. After the notification control unit notifies the user of the information and the second parallax image is acquired, the imaging condition determination unit may determine whether the imaging conditions have changed by determining whether the object distance measured by the object distance measurement unit has changed.

According to an eighth aspect of the present invention, in the fourth aspect, the notification control unit may notify the user of the information for encouraging the user to change the imaging conditions of the imaging unit to conditions different from the imaging conditions at the first timing.

According to a ninth aspect of the present invention, in the first aspect, the measurement apparatus may further include an imaging condition control unit which changes the imaging conditions of the imaging unit such that the measurement reliability increases after the reliability determination unit determines that the measurement reliability is low and before the second parallax image is acquired.

According to a tenth aspect of the present invention, in the ninth aspect, the imaging conditions may be at least one of the position of the imaging unit and the posture of the imaging unit.

According to an eleventh aspect of the present invention, in the tenth aspect, the imaging conditions may be an object distance between an optical system and the object. The optical system causes light from the object to enter the imaging unit.

According to a twelfth aspect of the present invention, in the ninth aspect, the imaging condition control unit may change the imaging conditions at the second timing to conditions different from the imaging conditions at the first timing.

According to a thirteenth aspect of the present invention, an operation method of a measurement apparatus includes a first imaging step, a display step, a designation point setting step, a first point detection step, a first reliability determination step, a first measurement step, an imaging condition determination step, a second imaging step, a second point detection step, a third point detection step, a second reliability determination step and a second measurement step. The measurement apparatus captures an image of an object which is a measurement target at a first timing and generates a first parallax image including two images having a parallax therebetween by an imaging unit in the first imaging step. The measurement apparatus causes a display unit to display at least one of the two images included in the first parallax image in the display step. The measurement apparatus sets a designation point in an image which is one of the two images included in the first parallax image and is displayed on the display unit in the designation point setting step. The measurement apparatus detects a corresponding point corresponding to the designation point in an image which is the other of the two images included in the first parallax image and differs from the image on which the designation point has been set in the first point detection step. The measurement apparatus determines a measurement reliability on the basis of the designation point and the corresponding point in the first reliability determination step. The measurement apparatus performs measurement of the object using the first parallax image in the first measurement step when the measurement reliability is determined to be high in the first reliability determination step. The measurement apparatus determines whether imaging conditions of the imaging unit have changed from imaging conditions at the first timing in the imaging condition determination step after the measurement reliability is determined to be low in the first reliability determination step. The measurement apparatus captures an image of the object at a second timing and generates a second parallax image including the two images by the imaging unit in the second imaging step after the measurement reliability is determined to be low in the first reliability determination step. The measurement apparatus detects a similar point in one of the two images included in the second parallax image in the second point detection step after it is determined that the imaging conditions have changed in the imaging condition determination step. The similar point is similar to the designation point set on one of the two images included in the first parallax image. The measurement apparatus detects a similar corresponding point corresponding to the similar point in an image which is the other of the two images included in the second parallax image and differs from the image in which the similar point is detected in the third point detection step. The measurement apparatus determines the measurement reliability on the basis of the similar point and the similar corresponding point in the second reliability determination step. The measurement apparatus performs measurement of the object using the second parallax image in the second measurement step, when the measurement reliability is determined to be high in the second reliability determination step.

DETAILED DESCRIPTION OF THE INVENTION

Hereinafter, embodiments of the present invention will be described with reference to the drawings. An example in which a measurement apparatus is an endoscope apparatus will be described below. The measurement apparatus may be an apparatus having a measurement function and is not limited to the endoscope apparatus.

First Embodiment

Figure 1:
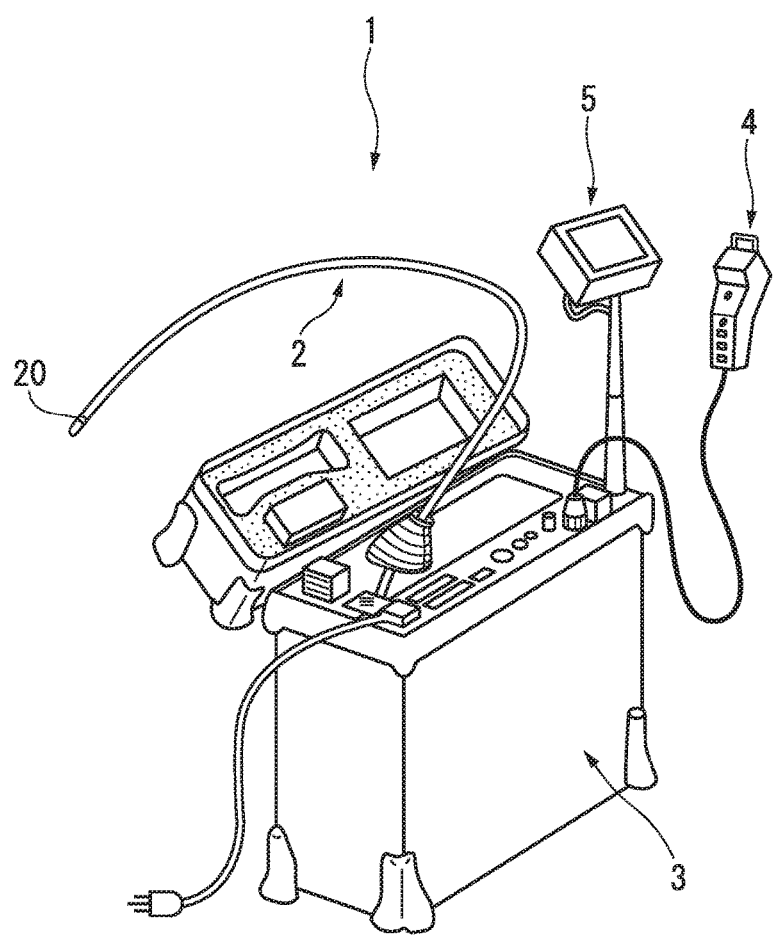
FIG. 1 is a perspective view showing the overall configuration of an endoscope apparatus according to a first embodiment of the present invention.

FIG. 1 shows the external appearance of an endoscope apparatus 1 (measurement apparatus) according to a first embodiment of the present invention. The endoscope apparatus 1 captures an image of a subject and measures geometric characteristics of the subject using the image. A user may change an optical adapter provided at the tip of an insertion part 2, select an embedded measurement processing program, and add a measurement processing program in order to perform observation and measurement of various subjects. Hereinafter, a case in which stereo measurement is performed will be described as an example of measurement.

As shown in FIG. 1, the endoscope apparatus 1 includes the insertion part 2, a main body 3, an operation unit 4, and a display unit 5.

The insertion part 2 is inserted into the inside of a subject. The insertion part 2 is a thin and long tube which is bendable from the tip 20 to the base end. The insertion part 2 captures an image of a measurement part and outputs an imaging signal to the main body 3. A stereo optical adapter 30 (FIG. 3) is provided at the tip 20 of the insertion part 2. The main body 3 is a control apparatus including a housing unit for housing the insertion part 2. The operation unit 4 receives an operation of a user with respect to the endoscope apparatus 1. The display unit 5 includes a display screen and displays an image of a subject captured by the insertion part 2, an operation menu and the like on the display screen.

The operation unit 4 is a user interface. For example, the user interface is at least one of a button, a switch, a key, a mouse, a joystick, a touch pad, a track ball and a touch panel. The display unit 5 is a monitor (display) such as a liquid crystal display (LCD).

Figure 2:
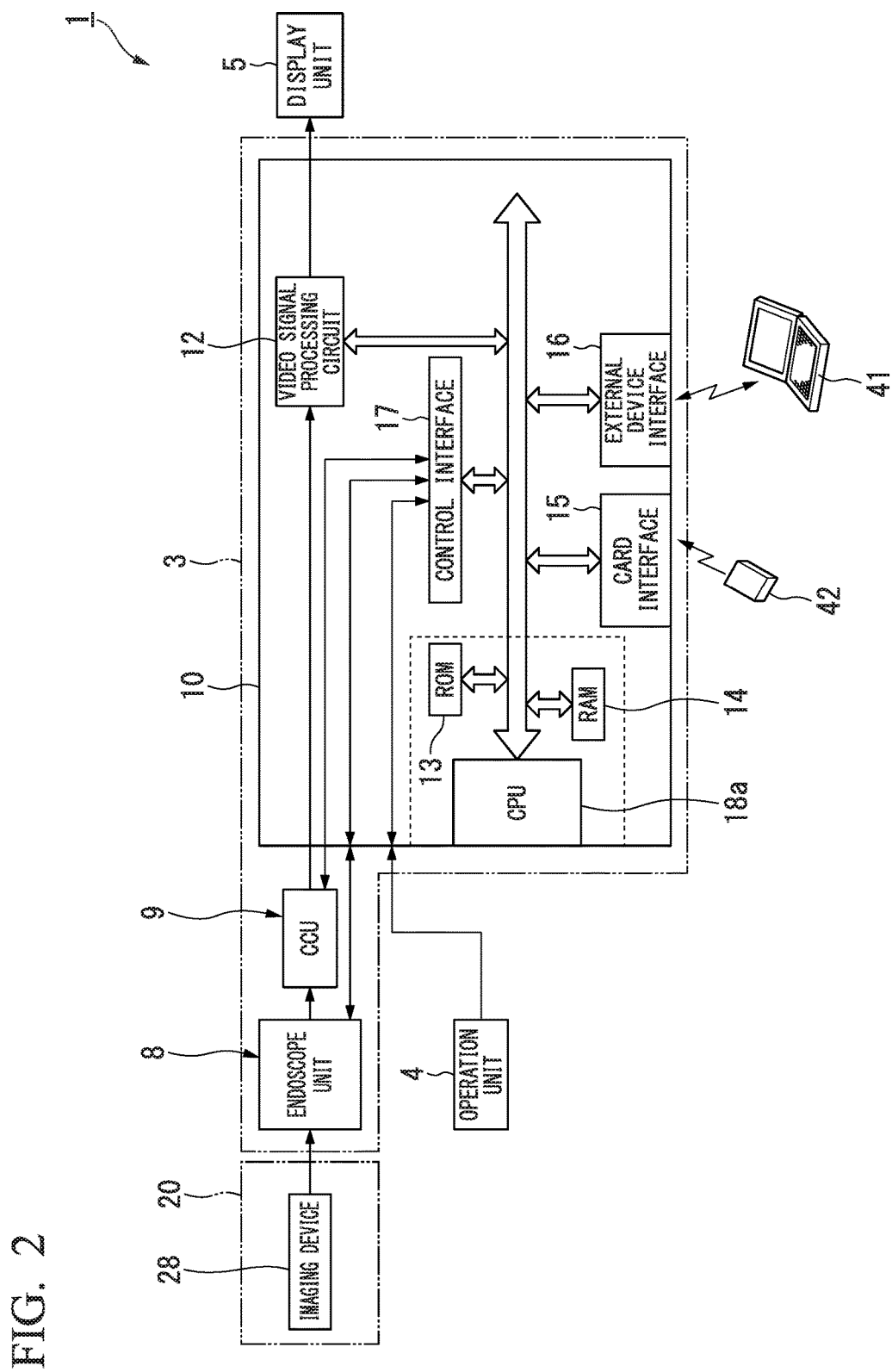
FIG. 2 is a block diagram showing an internal configuration of the endoscope apparatus according to the first embodiment of the present invention.

As shown in FIG. 2, the main body 3 includes an endoscope unit 8, a camera control unit (CCU) 9, and a control device 10. The endoscope unit 8 has a light source device and a bending device which are not shown. The light source device provides illumination light necessary for observation. The bending device bends a bending mechanism which is not shown. An imaging device 28 is included in the tip 20 of the insertion part 2. The imaging device 28 is an image sensor. The imaging device 28 photoelectrically converts a subject image formed through the stereo optical adapter 30 and generates an imaging signal. The CCU 9 drives the imaging device 28. The imaging signal output from the imaging device 28 is input to the CCU 9. The CCU 9 performs pre-processing including amplification, noise removal and the like on the imaging signal acquired by the imaging device 28. The CCP 9 converts the pre-processed imaging signal into a video signal such as an NTSC signal.

The control device 10 includes a video signal processing circuit 12, a read only memory (ROM) 13, a random access memory (RAM) 14, a card interface 15, an external device interface 16, a control interface 17 and a central processing unit (CPU) 18a.

The video signal processing circuit 12 performs predetermined video processing on a video signal output from the CCU 9. For example, the video signal processing circuit 12 performs video processing related to visibility enhancement. For example, such video processing includes color reproduction, grayscale correction, noise suppression, contour enhancement and the like. The video signal processing circuit 12 also performs processing for improving measurement accuracy when measurement is executed. For example, the video signal processing circuit 12 combines a video signal output from the CCU 9 and a graphic image signal generated by the CPU 18a. The graphic image signal includes an image of an operation screen, measurement information and the like. The measurement information includes a cursor image, an image of a designation point, a measurement result and the like. The video signal processing circuit 12 outputs the combined video signal to the display unit 5.

In addition, the video signal processing circuit 12 outputs image data based on the video signal output from the CCU 9 to the CPU 18a. Since the stereo optical adapter 30 is attached to the tip 20 of the insertion part 2 during measurement, the image based on the image data output from the video signal processing circuit 12 includes a plurality of subject images related to the same subject which is a measurement target. The plurality of subject images have different parallaxes. In an embodiment of the present invention, an example of using a method of simultaneously acquiring subject images formed by left and right optical systems will be described. The method of acquiring subject images is not limited thereto. For example, a method of acquiring a plurality of subject images having different parallaxes in a time divisional manner may be used. For example, any one of left and right optical paths of a stereo optical system is closed by a shutter and a subject image formed by light which has passed through the other optical path is captured. Subject images to be acquired are changed by changing a position closed by the shutter.

The ROM 13 is a nonvolatile recording medium in which a program used for the CPU 18*a* to control the operation of the endoscope apparatus 1 is recorded. The RAM 14 is a volatile recording medium in which information used by the CPU 18*a* to control the endoscope apparatus 1 is temporarily stored. The CPU 18*a* controls the operation of the endoscope apparatus 1 on the basis of the program recorded in the ROM 13.

A memory card 42 which is a detachable recording medium is connected to the card interface 15. The card interface 15 reads control processing information, image information and the like stored in the memory card 42 into the control device 10. In addition, the card interface 15 records control processing information, image information and the like generated by the endoscope apparatus 1 in the memory card 42.

An external device such as a USB device is connected to the external device interface 16. For example, a personal computer 41 is connected to the external device interface 16. The external device interface 16 transmits information to the personal computer 41 and receives information from the personal computer 41. Accordingly, a monitor of the personal computer 41 can display information. In addition, a user can perform operations with respect to control of the endoscope apparatus 1 through the personal computer 41.

The control interface 17 performs communication for operation control with the operation unit 4, the endoscope unit 8 and the CCU 9. The control interface 17 notifies the CPU 18*a* of an instruction input by a user through the operation unit 4. The control interface 17 outputs a control signal for controlling the light source device and the bending device to the endoscope unit 8. The control interface 17 outputs a control signal for controlling the imaging device 28 to the CCU 9.

A program executed by the CPU 18*a* may be recorded in a computer-readable recording medium. A computer external to the endoscope apparatus 1 may read and execute the program recorded in the recording medium. For example, the personal computer 41 may read and execute the program. The personal computer 41 may control the endoscope apparatus 1 by transmitting control information for controlling the endoscope apparatus 1 to the endoscope apparatus 1 in accordance with the program. Alternatively, the personal computer 41 may acquire a video signal from the endoscope apparatus 1 and perform measurement using the acquired video signal.

The aforementioned program may be transmitted to the endoscope apparatus 1 from a computer having a recording device or the like in which the program is stored through a transmission medium or transmitted waves in a transmission medium. A "transmission medium" transmitting a program is a medium having a function of transmitting information, such as a network (communication network) such as the Internet and a communication channel (communication line) such as a telephone line. Further, the aforementioned program may realize some of the above-described functions. In addition, the aforementioned program may be a differential file (differential program) which can be realized by combining the aforementioned functions with a program previously recorded in a computer.

Figure 3:
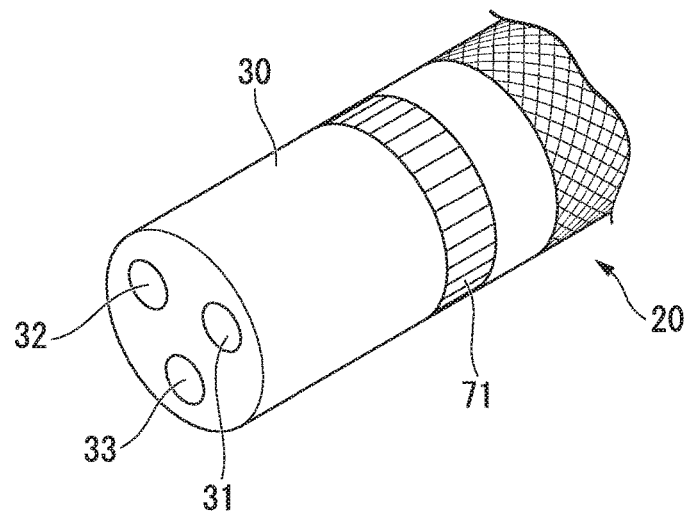
FIG. 3 is a perspective view showing configurations of the tip of an insertion part and a stereo optical adapter in the endoscope apparatus according to the first embodiment of the present invention.
Figure 4:
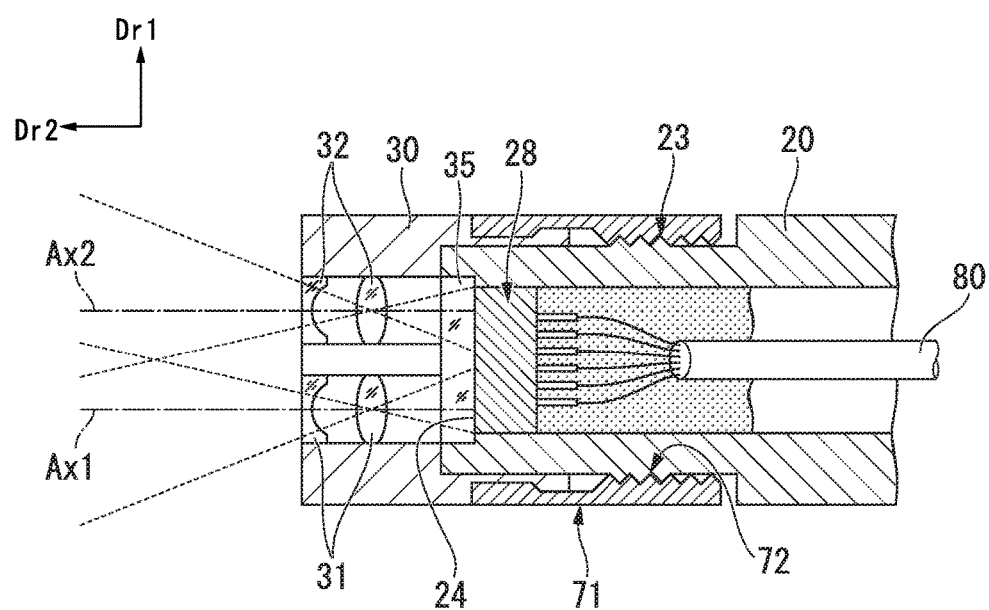
FIG. 4 is a cross-sectional view showing configurations of the tip of the insertion part and the stereo optical adapter in the endoscope apparatus according to the first embodiment of the present invention.

FIGS. 3 and 4 show configurations of the tip 20 of the insertion part 2 and the stereo optical adapter 30. FIG. 3 shows the external appearances of the tip 20 of the insertion part 2 and the stereo optical adapter 30. FIG. 4 shows a cross section of the tip 20 of the insertion part 2 and the stereo optical adapter 30. A cross section including a first optical system 31 and a second optical system 32 is shown in FIG. 4.

The stereo optical adapter 30 is attached to the tip 20 of the insertion part 2. The stereo optical adapter 30 is fixed to the tip 20 of the insertion part 2 by being screwed with a male screw 23 of the tip 20 of the insertion part 2 by means of a female screw 72 of a fixing ring 71. The first optical system 31, the second optical system 32 and an illumination window 33 are provided at a tip of the stereo optical adapter 30. The first optical system 31 and the second optical system 32 include objective lenses. The first optical system 31 and the second optical system 32 are separated from each other in a parallax direction Dr1. The first optical system 31 is disposed on the left side and the second optical system 32 is disposed on the right side when facing a subject. An optical axis Ax1 of the first optical system 31 and an optical axis Ax2 of the second optical system 32 are disposed in a direction Dr2 perpendicular to the parallax direction Dr1. That is, the optical axis Ax1 of the first optical system 31 and the optical axis Ax2 of the second optical system 32 are disposed such that they face in the direction Dr2. The parallax direction Dr1 is a direction of a straight line which passes through a first optical center (principal point) of the first optical system 31 and a second optical center (principal point) of the second optical system 32. The direction Dr2 is perpendicular to the parallax direction Dr1. The first optical system 31 and the second optical system 32 form two images of a subject on the imaging device 28 provided inside the tip 20 of the insertion part 2. The first optical system 31 forms a first optical image and the second optical system 32 forms a second optical image.

The first optical image and the second optical image have a parallax therebetween. The first optical system 31 may be disposed on the right side and the second optical system 32 may be disposed on the left side when facing a subject.

The imaging device 28 is provided at the tip 20 of the insertion part 2. The imaging device 28 has an imaging surface 24 disposed at imaging positions of the first optical system 31 and the second optical system 32. The imaging device 28 generates an imaging signal from a first optical image formed on the imaging surface 24 through the first optical system 31 and a second optical image formed on the imaging surface 24 through the second optical system 32. That is, the imaging device 28 generates a first image corresponding to the first optical image obtained through the first optical system 31 and a second image corresponding to the second optical image obtained through the second optical system 32. The first image and the second image have a parallax therebetween. In the first embodiment, an image corresponding to the left visual field is defined as the first image and an image corresponding to the right visual field is defined as the second image. An image corresponding to the right visual field may be defined as the first image and an image corresponding to the left visual field may be defined as the second image.

The imaging device 28 is connected to a signal line 80 and an imaging signal is output from the imaging device 28 to the signal line 80. A cover glass 35 for protecting the imaging device 28 is provided at the end face of the tip 20 of the insertion part 2.

As described above, the endoscope apparatus 1 includes the imaging device 28 (imaging unit), the CCU 9 (image acquisition unit) and the CPU 18a. The imaging device 28 captures an image of a subject which is an object corresponding to a measurement target and generates an imaging signal. Accordingly, the imaging device 28 generates a parallax image (stereo image) including two images having a parallax therebetween. The parallax image includes a pair of first images (a pair of left and right images acquired first) and a pair of second images (a pair of left and right images acquired second). The CCU 9 generates a video signal (image data) on the basis of the imaging signal. The video signal includes the image of the subject. Accordingly, the CCU 9 acquires the image of the subject which has been generated by capturing an image of the subject. The image acquired by the CCU 9 is input to the CPU 18a through the video signal processing circuit 12.

Figure 5:
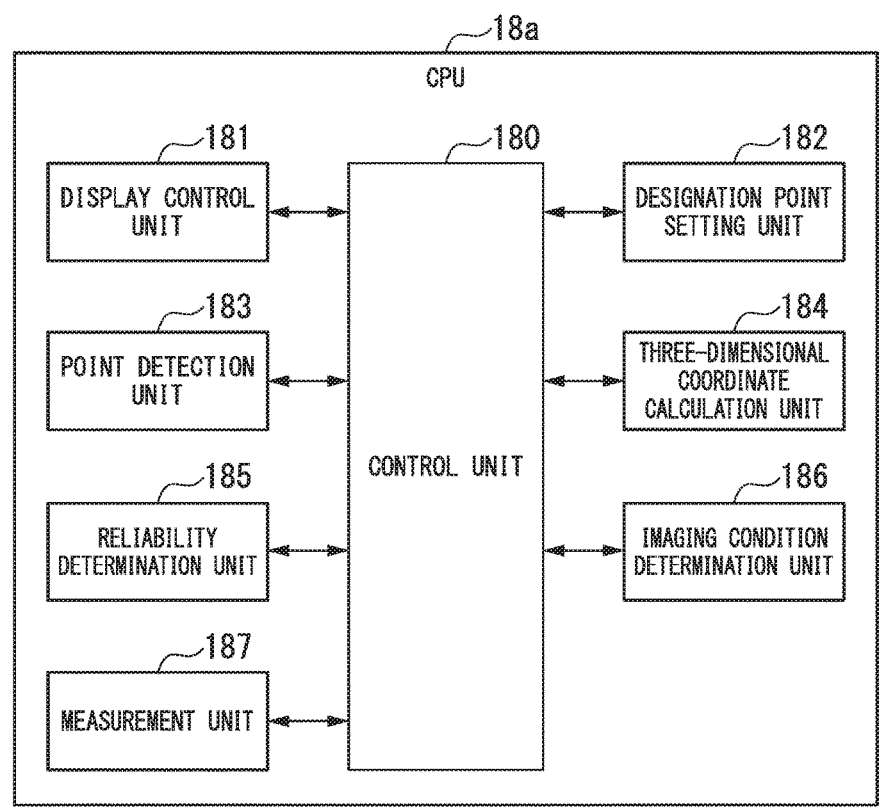
FIG. 5 is a block diagram showing a functional configuration of a CPU according to the first embodiment of the present invention.

FIG. 5 shows a functional configuration of the CPU 18a. Functions of the CPU 18a are constituted by a control unit 180, a display control unit 181, a designation point setting unit 182, a point detection unit 183, a three-dimensional coordinate calculation unit 184, a reliability determination unit 185, an imaging condition determination unit 186, and a measurement unit 187. At least one of the blocks shown in FIG. 5 may be constituted as a circuit separate from the CPU 18a.

Each unit shown in FIG. 5 may be constituted as at least one of a processor and a logic circuit. For example, the processor is at least one of a CPU, a digital signal processor (DSP) and a graphics processing unit (GPU). For example, the logic circuit is at least one of an application specific integrated circuit (ASIC) and a field-programmable gate array (FPGA). Each unit shown in FIG. 5 may include one or more processors. Each unit shown in FIG. 5 may include one or more logic circuits.

The control unit 180 controls a process performed by each unit. The display control unit 181 displays an image acquired by the CCU 9 on the display unit 5. At least one of a first image and a second image included in a parallax image generated by the imaging device 28 is displayed on the display unit 5. Accordingly, only one of the first image and the second image may be displayed on the display unit 5. Otherwise, the first image and the second image may be displayed on the display unit 5. The display control unit 181 displays a cursor used for a user to designate a designation point on an image. The display control unit 181 displays a mark or the like of a designation point designated by the user on an image.

For example, the display control unit 181 generates a graphic image signal such as a cursor. The display control unit 181 outputs the generated graphic image signal to the video signal processing circuit 12. The video signal processing circuit 12 combines a video signal output from the CCU 9 and the graphic image signal output from the CPU 18a. Accordingly, the cursor or the like is superimposed on an image. The video signal processing circuit 12 outputs the combined video signal to the display unit 5. The display unit 5 displays the image on which the cursor or the like is superimposed. The display control unit 181 detects a cursor movement instruction input by the user operating the operation unit 4 and sequentially updates the position of the cursor on the basis of the cursor movement instruction.

The designation point setting unit 182 sets one or more designation points in an image acquired by the CCU 9 and displayed on the display unit 5 on the basis of positions designated by the user in the image displayed on the display unit 5. The designation points are set in any one of the first image and the second image included in the parallax image.

The operation unit 4 receives a designation point input by the user operating the operation unit 4. The operation unit 4 outputs information indicating the position (coordinates) of the designation point designated by the user. The information output from the operation unit 4 is input to the control interface 17. The information input to the control interface 17 is input to the CPU 18a. The designation point setting unit 182 sets a designation point on the basis of the information input to the CPU 18a. Information on the set designation point is stored in the RAM 14. The designation point is set by correlating the position of the designation point with a specific image.

A designation point is coordinate information on a position of interest in an image determined by an instruction of the user. The designation point indicates a measurement position on a subject. In addition, the designation point indicates a position at which a measurement reliability is calculated in an image.

The point detection unit 183 searches for and detects a corresponding point in the other image that corresponds to a designation point set in one of two images included in a parallax image. Generally, this process is called a matching process. When a designation point is set in the first image, the point detection unit 183 detects a corresponding point in the second image. When a designation point is set in the second image, the point detection unit 183 detects a corresponding point in the first image.

In addition, the point detection unit 183 searches for and detects a similar point in a second parallax image different from a first parallax image that is similar to a designation point set in the first parallax image. The similar point is detected from an image having the same parallax relationship as an image in which the designation point is set. When a designation point is set in the first image of the first parallax image, a similar point in the first image of the second parallax image is detected. When a designation point is set in the second image of the first parallax image, a similar point in the second image of the second parallax image is detected.

Further, the point detection unit 183 searches for and detects a corresponding point (similar corresponding point) in the other image that corresponds to a similar point detected from one of two images included in a parallax image through a matching process. When a similar point is detected from the first image, the point detection unit 183 detects a similar corresponding point in the second image. When a similar point is detected from the second image, the point detection unit 183 detects a similar corresponding point in the first image.

The three-dimensional coordinate calculation unit 184 calculates three-dimensional coordinates (spatial coordinates) of each of designation points and similar points using an image acquired by the CCU 9. Specifically, the three-dimensional coordinate calculation unit 184 calculates a parallax quantity using coordinates of designation points and corresponding points. Otherwise, the three-dimensional coordinate calculation unit 184 calculates a parallax quantity using coordinates of similar points and similar corresponding points. The three-dimensional coordinate calculation unit 184 calculates three-dimensional coordinates of a designation point or a similar point on the basis of the calculated parallax quantity and camera calibration information. The camera calibration information is also called a camera parameter. The camera calibration information is generated when factory shipment is performed or the optical adapter is attached to the tip 20 of the insertion part 2.

The reliability determination unit 185 calculates a measurement reliability at a designation point or a similar point on the basis of pixel information around the designation point or the similar point or on the basis of three-dimensional coordinates (including generated intermediate data such as a matching correlation value) calculated by the three-dimensional coordinate calculation unit 184. The reliability determination unit 185 determines a measurement reliability by comparing a calculated reliability with a previously stored reference value (threshold value).

The imaging condition determination unit 186 determines whether imaging conditions of the imaging device 28 have changed. For example, the imaging conditions are at least one of the position and the posture of the imaging device 28. The imaging conditions may be an object distance between an object and an optical system which causes light from the object that is a measurement target to enter the imaging device 28. The optical system which causes light from the object that is a measurement target to enter the imaging device 28 is the first optical system 31 and the second optical system 32 in the stereo optical adapter 30. The object distance is a distance between the optical system and a point on the object which corresponds to a designation point. For example, the imaging condition determination unit 186 determines whether imaging conditions have changed by determining whether the imaging device 28 has been moved.

The measurement unit 187 measures an object through stereo measurement using a parallax image. That is, the measurement unit 187 measures the size of a three-dimensional shape of the object. The measurement unit 187 may include the three-dimensional coordinate calculation unit 184.

A schematic operation of the endoscope apparatus 1 constituted as described above will be described. The imaging device 28 captures an image of an object which is a measurement target at a first timing and generates a first parallax image including two images having a parallax therebetween. When the two images are generated in a time divisional manner, the first timing includes an imaging timing of the first image and an imaging timing of the second image. The first timing may be any one imaging timing which is a reference between the imaging timing of the first image and the imaging timing of the second image. The first timing may be an intermediate timing of the imaging timing of the first image and the imaging timing of the second image, or the like.

The display control unit 181 displays, on the display unit 5, at least one of the two images included in the first parallax image generated when the image of the object is captured at the first timing. The designation point setting unit 182 sets a designation point on the image which is one of the two images included in the first parallax image and is displayed on the display unit 5. The point detection unit 183 detects a corresponding point corresponding to the designation point in an image which is the other of the two images included in the first parallax image and differs from the image having the designation point set therein. The reliability determination unit 185 determines a measurement reliability on the basis of the designation point and the corresponding point.

When the reliability determination unit 185 determines that the measurement reliability is high, the measurement unit 187 measures the object using the parallax image.

After the reliability determination unit 185 determines that the measurement reliability is low, the imaging condition determination unit 186 determines whether imaging conditions of the imaging device 28 have changed from imaging conditions at the first timing. After the reliability determination unit 185 determines that the measurement reliability is low, the imaging device 28 captures an image of the object which is the measurement target at a second timing and generates a second parallax image including two images having a parallax therebetween. After the imaging condition determination unit 186 determines that the imaging conditions have changed, the point detection unit 183 detects a similar point in one of the two images included in the second parallax image. The similar point is similar to the designation point set in one of the two images included in the first parallax image. The point detection unit 183 detects a similar corresponding point corresponding to the similar point in an image which is the other of the two images included in the second parallax image and differs from the image in which the similar point has been detected. The reliability determination unit 185 determines a measurement reliability on the basis of the similar point and the similar corresponding point.

Figure 6:
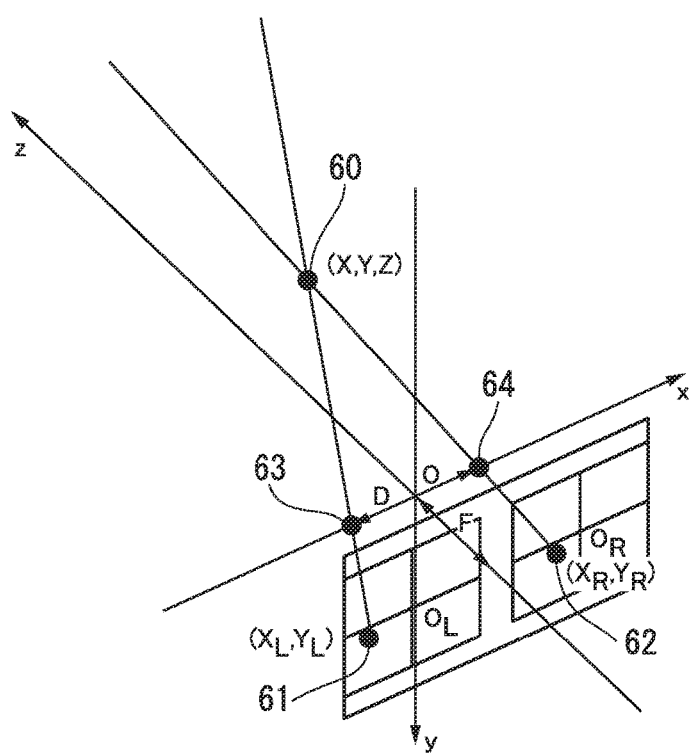
FIG. 6 is a reference diagram for describing a method of calculating three-dimensional coordinates of a measurement designation point according to stereo measurement of the first embodiment of the present invention.

The principle of stereo measurement will be described with reference to FIG. 6. In stereo measurement, three-dimensional coordinates of a subject are calculated using the principle of triangulation on the basis of coordinates of two optical ranging points when a subject image is captured using two optical systems. The center point of a segment which connects a left optical center (first optical center 63) and a right optical center (second optical center 64) is defined as an origin O. In addition, an x axis having the right direction as the positive direction and a y axis having the downward direction as the positive direction are defined. Further, a z axis having a direction away from an optical system in parallel with the optical axis as the positive direction is defined.

Three-dimensional coordinates (X, Y, Z) of a measurement designation point 60 are calculated for images including subject images obtained through a left optical system and a right optical system through the following equations (1) to (3) according to the principle of triangulation. Here, two-dimensional coordinates of a measurement designation point 61 of a distortion-corrected left image face and a corresponding point 62 of a distortion-corrected right image face are $(X_L, Y_L)$ and $(X_R, Y_R)$, respectively. The origins of the two-dimensional coordinates are intersections $O_L$ and $O_R$ of the optical axes of the left optical system and the right optical system and the image surfaces, respectively. The distance between the first optical center 63 and the second optical center 64 is D. A focal distance is F. A parameter t is $D/(X_R - X_L)$.

$$X = t \times X_R + D/2 \quad (1)$$

$$Y = -t \times Y_R \quad (2)$$

$$Z = t \times F \quad (3)$$

When the coordinates of the measurement designation point 61 and the corresponding point 62 on the image surfaces are determined as described above, the three-dimensional coordinates of the measurement designation point 60 can be obtained using the parameter D and the parameter F. Various measurement functions may be realized by obtaining three-dimensional coordinates of several points. For example, a distance between two points, a distance between a line which connects the two points and one point, the area of a region surrounded by a line which connects a plurality of points, the depth of a reference surface, a surface shape and the like are measured. A user can select a desired measurement function from the various measurement functions. In addition, a distance (object distance) between the first optical center 63 or the second optical center 64 and a subject may be obtained. To perform the above-described stereo measurement, optical data indicating characteristics of the optical system including the tip 20 of the insertion part 2 and the stereo optical adapter 30 is needed. For example, the matching process and details of the optical data are disclosed in Japanese Unexamined Patent Application, First Publication No. 2004-49638 and thus a description thereof is omitted.

Figure 7:
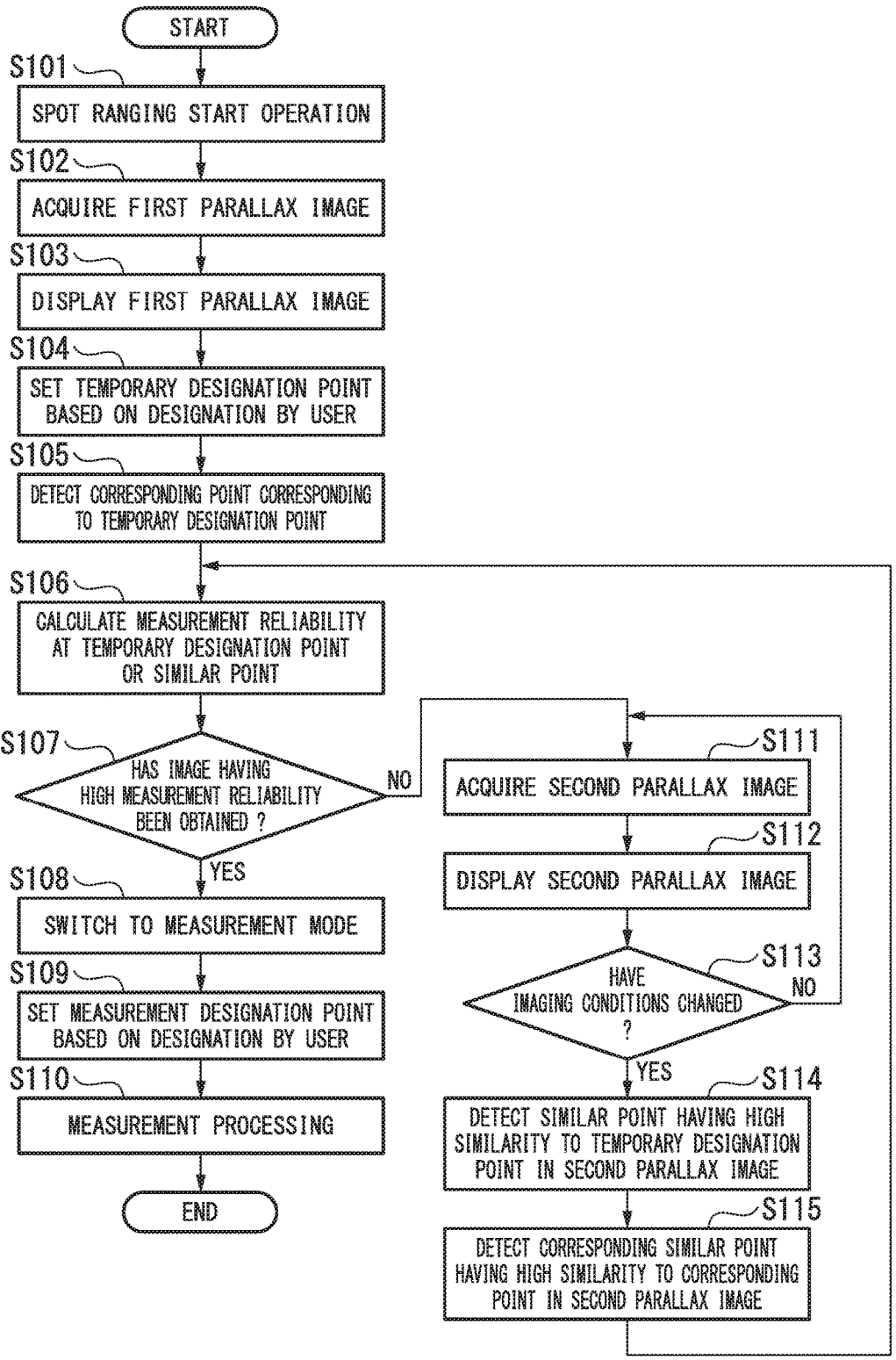
FIG. 7 is a flowchart showing a procedure of processes for measurement in the first embodiment of the present invention.
Figure 8:
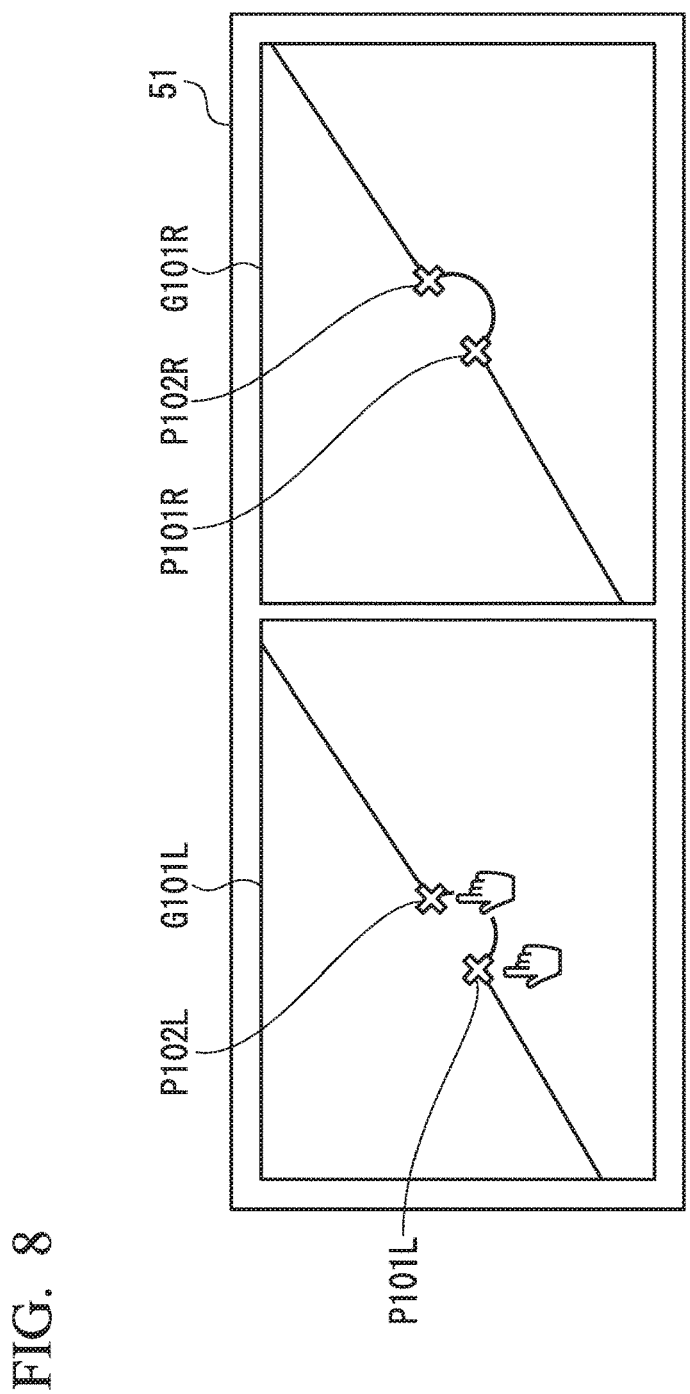
FIG. 8 is a diagram showing a display screen of a display unit in the first embodiment of the present invention.

A series of flow from initiation of measurement to execution of a measurement process will be described with reference to FIGS. 7 to 10. FIG. 7 shows processes for measurement. FIG. 8 shows a display screen 51 of the display unit 5. FIG. 9 and FIG. 10 show acquired images.

In endoscopy, a user checks a situation of a subject through a live image and inspects whether there is a defect or damage. Here, the endoscope apparatus 1 operates in an observation mode. When a defect or damage which is a measurement target is discovered from the subject, the state of the endoscope apparatus 1 changes from the observation mode to a spot ranging mode or a measurement mode. In the spot ranging mode, the endoscope apparatus 1 receives a designation point on a live image from the user and displays a ranging result of the designation point on a screen in real time. The ranging result represents the depth from the optical system to an arbitrary point on the subject, that is, an object distance. A description of a ranging process and ranging result display in the spot ranging mode is omitted.

In the measurement mode, the endoscope apparatus 1 acquires a still image on the basis of an image acquisition operation performed by the user in the observation mode or the stop ranging mode and performs dimension measurement using the still image. The image acquisition operation is also called "freeze." In the following, it is assumed that an operation for switching from the observation mode to the spot ranging mode is performed.

The user performs a spot ranging start operation by operating the operation unit 4 (step S101).

After step S101, the control unit 180 instructs the CCU 9 to acquire a first parallax image necessary for three-dimensional measurement. The CCU 9 drives the imaging device 28 such that the imaging device 28 captures an image of a subject and generates the first parallax image. The CCU 9 acquires the first parallax image from the imaging device 28. The acquired first parallax image is output to the display unit 5 and the CPU 18*a* through the video signal processing circuit 12 (step S102). Step S102 corresponds to a first imaging step.

After step S102, the display control unit 181 causes the display unit 5 to display the first parallax image acquired by the CCU 9 (step S103). In step S103, a first image and a second image included in the first parallax image are displayed on the display unit 5. Only any one of the first image and the second image may be displayed on the display unit 5. Step S103 corresponds to a display step.

After step S103, the user designates a temporary designation point in the displayed image by operating the operation unit 4. Here, the temporary designation point is designated in any one of the first image and the second image included in the first parallax image. The operation unit 4 receives the temporary designation point designated by the user. The designation point setting unit 182 sets the temporary designation point designated by the user in the displayed image (step S104). Step S104 corresponds to a designation point setting step.

The temporary designation point represents a region of interest that the user intends to measure. In addition, the temporary designation point represents a reference position for calculating measurement reliability. A designation point designated by the user includes the temporary designation point and a measurement designation point. In the following description, the temporary designation point is distinguished from the measurement designation point designated in a measurement process but the temporary designation point may be used as the measurement designation point. Although an example in which the temporary designation point is set in the first image included in the first parallax image will be described below, the temporary designation point may be set in the second image included in the first parallax image.

Although the word "point" is used in the present description for convenience, a designation point need not be one point corresponding to one pixel on a screen. A designation point may include a region having any shape and size. The shape of the region may be a circle, a rectangle and the like. The shape and size of the region may be arbitrarily changed by the user. Although two temporary designation points are designated in the example shown in FIG. 8, two points need not be designated. One designated point may have a certain region and a region of interest may be covered by only the point. Of course, two or more points may be designated.

FIG. 8 shows a display screen 51 of the display unit 5. As shown in FIG. 8, the first image G101L and the second image G101R included in the first parallax image are displayed. In this example, two temporary designation points P101L and P102L are set in the first image G101L. When each temporary designation point has been designated by an operation performed by the user, the designation point setting unit 182 calculates each position (coordinates) of each designated temporary designation point. Position information (coordinate information) on each temporary designation point is stored in the RAM 14.

The two set temporary designation points P101L and P102L are displayed on the display unit 5. The display control unit 181 causes the display unit 5 to display each temporary designation point. Specifically, the display control unit 181 generates a graphic image signal of each temporary designation point. The display control unit 181 outputs the generated graphic image signal to the video signal processing circuit 12. The video signal processing circuit 12 combines a video signal output from the CCU 9 and the graphic image signal output from the CPU 18*a*. Accordingly, each temporary designation point is superimposed on the first image. The video signal processing circuit 12 outputs the combined video signal to the display unit 5. The display unit 5 displays the first image on which each temporary designation point has been superimposed. Accordingly, the user can recognize the position of each temporary designation point.

After step S104, the point detection unit 183 searches for and detects corresponding points corresponding to the temporary designation points in the second image of the first parallax image through a matching process (step S105). A process called template matching is often used as the matching process. Any matching process may be used as long as corresponding points corresponding to the temporary designation points can be found. Step S105 corresponds to a first point detection step.

In the example shown in FIG. 8, two corresponding points P101R and P102R in the second image G101R are detected. Position information (coordinate information) on each corresponding point is stored in the RAM 14.

The two detected corresponding points P101R and P102R are displayed on the display unit 5. The display control unit 181 causes the display unit 5 to display each corresponding point. Specifically, the display control unit 181 generates a graphic image signal of each corresponding point. The display control unit 181 outputs the generated graphic image signal to the video signal processing circuit 12. The video signal processing circuit 12 combines the video signal output from the CCU 9 and the graphic image signal output from the CPU 18a. Accordingly, each corresponding point is superimposed on the second image. The video signal processing circuit 12 outputs the combined video signal to the display unit 5. The display unit 5 displays the second image on which each corresponding point is superimposed. Accordingly, the user can recognize the position of each corresponding point.

After step S105, the three-dimensional coordinate calculation unit 184 calculates three-dimensional coordinates of the temporary designation points. After the three-dimensional coordinates are calculated, the reliability determination unit 185 calculates a measurement reliability (step S106). Pixel values of a two-dimensional image around the temporary designation points and the corresponding points, intermediate data obtained in a process of calculating the three-dimensional coordinates of the temporary designation points, the three-dimensional coordinates of the temporary designation points, a spatial resolution determined by the principle of triangulation, and the like are used for calculation of the measurement reliability.

A case in which pixel values of the two-dimensional image around the temporary designation points or the corresponding points are used will be described. For example, the reliability determination unit 185 calculates a measurement reliability on the basis of the luminance (brightness) of pixels around the temporary designation points and the luminance (brightness) of pixels around the corresponding points. Otherwise, the reliability determination unit 185 calculates a measurement reliability on the basis of a difference of the pattern of a subject between the temporary designation points and a surrounding region thereof and a difference of the pattern of the subject between the corresponding points and a surrounding region thereof. A difference of the pattern of the subject is detected on the basis of colors, luminance and the like.

A case in which the intermediate data obtained in the process of calculating the three-dimensional coordinates of the temporary designation points are used will be described. For example, the reliability determination unit 185 calculates a measurement reliability on the basis of a matching correlation value, a form of an evaluation function, and the like.

A case in which a spatial resolution determined according to the principle of triangulation is used will be described. For example, the reliability determination unit 185 calculates a measurement reliability on the basis of a base length, a focal distance and a ranging value. The base length and the focal distance are determined according to design values or estimated in advance according to camera calibration. The ranging value is a z coordinate of calculated three-dimensional coordinates.

An example of a specific method of calculating a measurement reliability will be described. For example, the reliability determination unit 185 calculates a final measurement reliability E using a weighted linear sum as represented by Equation (4) for reliability values calculated from various factors.

$$E_{P101L} = \Sigma_{i=0}^{N} w_i e_i \qquad (4)$$

Equation (4) represents a measurement reliability E at the temporary designation point P101L. $e_i$ in Equation (4) denotes a reliability value of each factor. $w_i$ in Equation (4) denotes a weight quantity of each factor. N in Equation (4) indicates the number of assumed factors. A measurement reliability E at the temporary designation point P102L is also calculated through the same operation as Equation (4). The reliability determination unit 185 may calculate the final measurement reliability by summing up all measurement reliabilities of the temporary designation point P101L and the temporary designation point P102L.

The measurement reliability calculation method is not limited to the above-described method. For example, there may be a plurality of types of measurement reliability. The measurement reliability calculation method may be a logical operation of a reliability value of each factor. Otherwise, the minimum value of reliability values with respect to assumed factors may be used as the final measurement reliability E. A processing unit separate from the reliability determination unit 185 may calculate an index indicating a measurement reliability and the reliability determination unit 185 may determine the measurement reliability on the basis of the index.

After step S106, the reliability determination unit 185 determines whether the first parallax image acquired in step S102 is suitable for measurement by comparing the calculated measurement reliability with a previously stored threshold value. That is, the reliability determination unit 185 determines whether the measurement reliability is high (step S107). Step S107 corresponds to a first reliability determination step.

For example, when the calculated measurement reliability is higher than the threshold value, the reliability determination unit 185 determines that the measurement reliability is high. When the calculated measurement reliability is lower than the threshold value, the reliability determination unit 185 determines that the measurement reliability is low.

When the reliability determination unit 185 determines that the measurement reliability is high in step S107, the state of the endoscope apparatus 1 switches to a state for performing measurement on the parallax image. A process executed in that state is the same as the process of the measurement mode. The user selects the measurement mode through the operation unit 4 (step S108).

The measurement mode is a mode in which distance measurement between two points, line based measurement, surface based measurement and the like are executed. In the distance measurement between two points, a three-dimensional distance between two measurement designation points designated by a user is measured. In the line based measurement, a reference line is set on the basis of two reference points designated by a user and a three-dimensional distance from a measurement designation point designated by the user to the reference line is measured. In the surface based measurement, a reference plane is set on the basis of three reference points designated by a user and a three-dimensional distance (the length of a perpendicular line) from a measurement designation point designated by the user to the reference plane is measured.

After step S108, the user operates the operation unit 4 to adjust the coordinates designated as the temporary designation points in units of a subpixel. Accordingly, the user determines a final measurement designation point indicating a measurement position. The operation unit 4 receives the measurement designation point determined by the user. The designation point setting unit 182 sets the measurement designation point determined by the user on the displayed image (step S109). In step S109, one or more measurement designation points are set.

After step S109, the measurement process is executed (step S110). The process in step S110 is a general stereo measurement process. In step S110, the point detection unit 183 searches for and detects measurement corresponding points corresponding to measurement designation points through a matching process. The three-dimensional coordinate calculation unit 184 calculates three-dimensional coordinates of the measurement designation points on the basis of the coordinates of the measurement designation points and the measurement corresponding points. The measurement unit 187 measures the object on the basis of the three-dimensional coordinates of the measurement designation points. The display control unit 181 causes the display unit 5 to display a measurement result. Step S110 corresponds to a first measurement step.

When the reliability determination unit 185 determines that the measurement reliability is low in step S107, the control unit 180 instructs the CCU 9 to acquire a second parallax image necessary for three-dimensional measurement. The CCU 9 drives the imaging device 28 such that the imaging device 28 captures an image of the subject to generate the second parallax image. The CCU 9 acquires the second parallax image from the imaging device 28. The acquired second parallax image is output to the display unit 5 and the CPU 18a through the video signal processing circuit 12 (step S111). The first parallax image and the second parallax image are generated at different timings. Step S111 corresponds to a second imaging step.

After step S111, the display control unit 181 causes the display unit 5 to display the second parallax image acquired by the CCU 9 (step S112). In step S112, a first image and a second image included in the second parallax image are displayed on the display unit 5. Only one of the first image and the second image may be displayed on the display unit 5.

After step S112, the imaging condition determination unit 186 compares the first parallax image acquired in step S102 with the second parallax image acquired in step S111. Accordingly, the imaging condition determination unit 186 determines whether the imaging conditions have changed (step S113). In the first embodiment, the imaging condition determination unit 186 determines whether the imaging conditions of the imaging device 28 have changed from imaging conditions at the first timing after the second parallax image is generated. Here, the imaging condition determination unit 186 determines whether imaging conditions at the second timing have changed from the imaging conditions at the first timing. Step S113 corresponds to an imaging condition determination step.

In this example, the imaging condition determination unit 186 determines imaging condition change through image comparison. An example of a specific method will be described. The imaging condition determination unit 186 calculates a difference between each pixel of the first image of the first parallax image and each pixel of the first image of the second parallax image. The imaging condition determination unit 186 may calculate a difference between each pixel of the second image of the first parallax image and each pixel of the second image of the second parallax image. The imaging condition determination unit 186 adds up absolute values of differences between respective pixels. The imaging condition determination unit 186 determines whether the sum of the absolute values of the differences exceeds a threshold value. When the sum of the absolute values of the differences exceeds the threshold value, the imaging condition determination unit 186 determines that the imaging conditions have changed. When the sum of the absolute values of the differences does not exceed the threshold value, the imaging condition determination unit 186 determines that the imaging conditions have not changed.

The imaging condition determination method is not limited to the above-described method. Any method may be used as long as it can be determined whether the imaging conditions have changed using the first parallax image and the second parallax image. As will be described in a fourth modified example of the first embodiment, imaging condition determination may be performed through a method which does not perform image comparison. The fourth modified example of the first embodiment will be described later.

The three-dimensional coordinate calculation unit 184 calculates the three-dimensional coordinates of the temporary designation points in step S106. The z coordinate constituting the calculated three-dimensional coordinates represents the object distance. Accordingly, the three-dimensional coordinate calculation unit 184 measures the object distance in step S106. In step S113, the imaging condition determination unit 186 may determine whether the imaging conditions have changed by determining whether the object distance measured by the three-dimensional coordinate calculation unit 184 has changed.

When the imaging condition determination unit 186 determines that the imaging conditions have not changed in step S113, the process in step S111 is executed. That is, when the imaging conditions have not changed, the second parallax image is repeatedly acquired. The processes shown in FIG. 7 do not include a process for encouraging the user to change the imaging conditions or a process through which the endoscope apparatus 1 intentionally changes the imaging conditions. In an endoscopy environment, there are many cases in which at least one of the position and the posture of the tip 20 of the insertion part 2 constantly changes due to a factor such as hand shake, gravity or the like. That is, at least one of the position and the posture of the imaging device 28 is easily changed according to the surrounding environment of the imaging device 28. Accordingly, the processes from step S111 to step S113 are rarely continuously executed. If the imaging conditions do not change even when a certain time has elapsed, the spot ranging mode may be ended.

When the imaging condition determination unit 186 determines that the imaging conditions have changed in step S113, the point detection unit 183 searches for and detects similar points similar to temporary designation points in the first image of the second parallax image (step S114). Step S114 corresponds to a second point detection step.

Figure 9A:
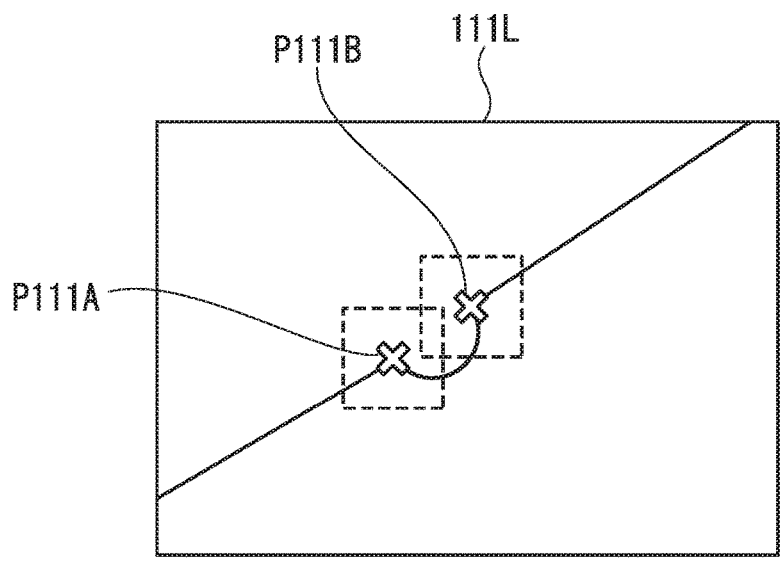
FIG. 9A is a diagram showing images acquired in the first embodiment of the present invention.
Figure 9B:
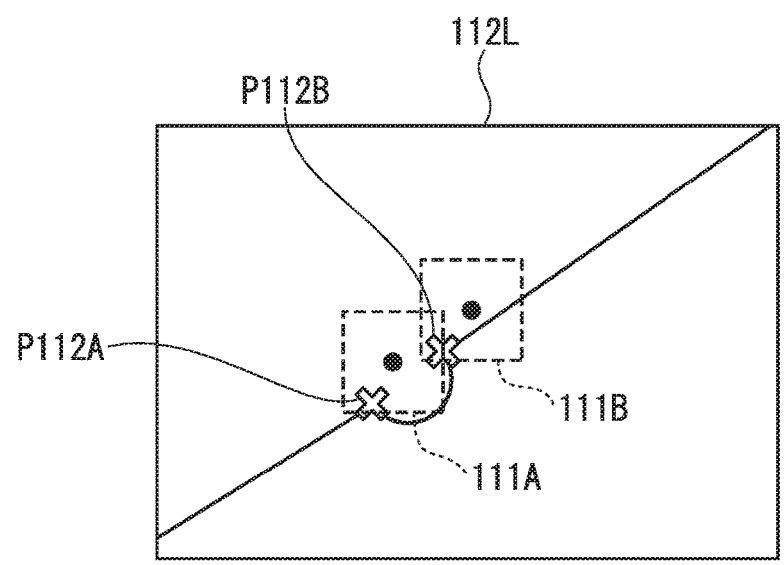
FIG. 9B is a diagram showing images acquired in the first embodiment of the present invention.

The process in step S114 will be described in detail using FIGS. 9A and 9B. FIG. 9A shows the first image 111L of the first parallax image. FIG. 9B shows the first image 112L of the second parallax image. The position of a region in which the user is interested on the first image 111L slightly differs from that on the first image 112L. Specifically, the region of interest in the first image 112L is deviated from the region of interest in the first image 111L in a lower left direction in FIG. 9B.

The coordinates of temporary designation points P111A and P111B on the first image 111L are stored in the RAM 14. The point detection unit 183 sets a region of interest (ROI) 111A and a ROI 111B having the coordinates of the temporary designation points as centers in the first image 112L. The point detection unit 183 determines a similar point P112A which is a point most similar to the temporary designation point P111A in the ROI 111A. In the same manner, the point detection unit 183 determines a similar point P112B which is a point most similar to the temporary designation point P111B in the ROI 111B.

As a method for determining a similar point, known technologies such as template matching, Kanade-Lucas-Tomasi Feature Tracker (KLT) and Particle Filter may be used. Methods for determining a similar point are not limited thereto. Any method may be used as long as coordinates of a similar point on the first image (or the second image) of the second parallax image can be obtained from coordinates of a temporary designation point on the first image (or the second image) of the first parallax image.

After step S114, the point detection unit 183 searches for and detects similar corresponding points corresponding to the similar points in the second image of the second parallax image (step S115). For example, the same process as the process in step S114 is executed in step S115. Step S115 corresponds to a third point detection step.

Figure 10A:
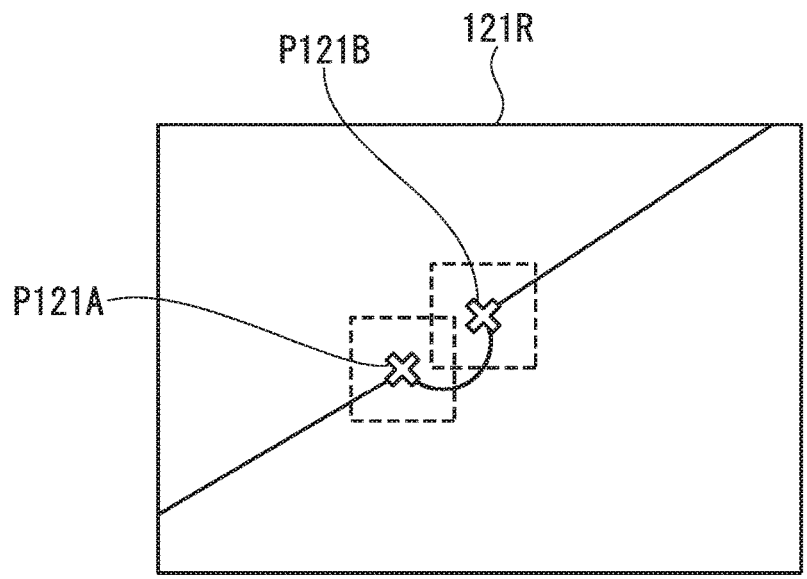
FIG. 10A is a diagram showing images acquired in the first embodiment of the present invention.
Figure 10B:
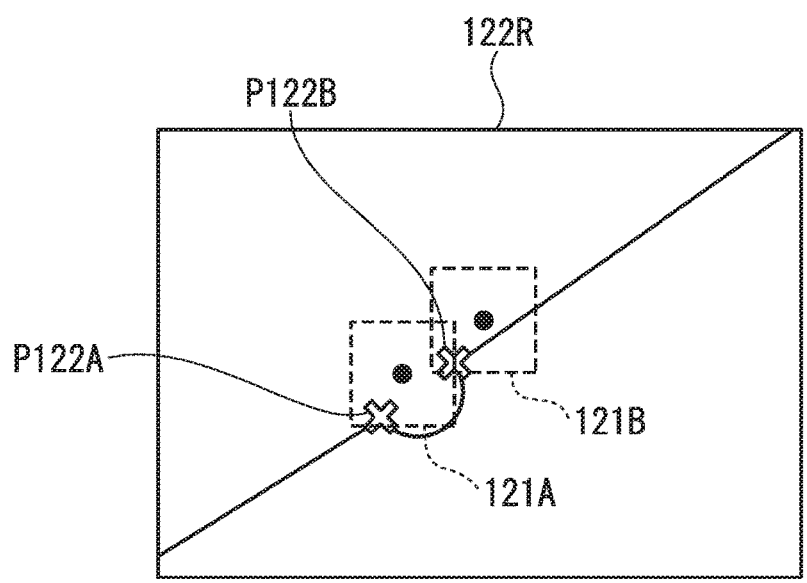
FIG. 10B is a diagram showing images acquired in the first embodiment of the present invention.

The process in step S115 will be described in detail using FIGS. 10A and 10B. FIG. 10A shows the second image 121R of the first parallax image. FIG. 10B shows the second image 122R of the second parallax image.

The coordinates of a corresponding point P121A and a corresponding point P121B detected from the second image 121R are stored in the RAM 14. The point detection unit 183 sets a ROI 121A and a ROI 121B having the coordinates of the corresponding points as centers in the second image 122R. The point detection unit 183 determines a similar corresponding point P122A which is a point most similar to the corresponding point P121A in the ROI 121A. In the same manner, the point detection unit 183 determines a similar corresponding point P122B which is a point most similar to the corresponding point P121B in the ROI 121B.

The process for detecting a similar corresponding point is not limited to the above-described process. For example, the point detection unit 183 may detect similar corresponding points on the second image of the second parallax image through a matching process on the basis of similar points detected from the first image of the second parallax image. This process is the same as the first point detection step corresponding to step S105.

After step S115, the process in step S106 is executed. In step S106, the temporary designation points are replaced by the similar points and a measurement reliability at the similar points is calculated. Thereafter, the measurement reliability is determined in step S107 (second reliability determination step). When the reliability determination unit 185 determines that the measurement reliability is high, the processes in step S108 and step S109 are executed. Then, the measurement process in step S110 (second measurement step) is executed.

According to the above-described processes, a pair of parallax images is continuously acquired until the measurement reliability becomes high. The processes may be ended when an image having a high measurement reliability has not been acquired within a predetermined time limit.

The process in step S112 is not necessary. Accordingly, the second parallax image need not be displayed.

The mode in which the characteristic processes shown in FIG. 7 are executed is not limited to the spot ranging mode. Accordingly, the process in step S101 is not necessary.

When the measurement mode is set in advance, the characteristic processes shown in FIG. 7 may be executed. Accordingly, the process in step S108 is not necessary.

The process in step S109 is not necessary as will be described in a second modified example of the first embodiment.

When the measurement reliability of acquired parallax images is low in the first embodiment, it is determined whether imaging conditions have changed. After change of the imaging conditions is confirmed, the parallax images are acquired again. Accordingly, the number of times of acquiring parallax images can be reduced. Therefore, the endoscope apparatus 1 can reduce user's labor and acquire an image having a high measurement reliability. As a result, inspection efficiency is improved.

In a conventional technology in which a plurality of images are acquired before a user designates designation points, it is necessary to store the plurality of acquired images in a storage region such as a memory until measurement is executed. When a large number of images are acquired, there is a problem that many hardware resources are used. This may become a considerable restriction when characteristics of built-in equipment are considered. In the first embodiment, it is possible to save hardware resources for storing images because the number of acquired parallax images is reduced.

First Modified Example of First Embodiment

In the above-described example, one pair of second parallax images is acquired in step S111. However, one pair of second parallax images need not be acquired in step S111. In the first modified example of the first embodiment, N pairs of second parallax images are continuously acquired when the process in step S111 is executed once. N is an integer equal to or greater than 2. In step S112, images included in the N pairs of parallax images are simultaneously displayed on the display unit 5. Alternatively, the images included in the N pairs of parallax images are sequentially displayed on the display unit 5 pair by pair in step S112.

The reliability determination unit 185 may determine whether the imaging conditions have changed from imaging conditions of the first parallax image for each of the acquired N pairs of second parallax images. When the imaging conditions have changed, the processes in steps S114, S115, S106 and S107 may be executed for each of the acquired second parallax images. Consequently, a plurality of second parallax images having high measurement reliabilities may be extracted. In such a case, one pair of second parallax images having the highest measurement reliability among the extracted second parallax images may be used for measurement.

When measurement reliabilities are determined to be high for the plurality of second parallax images in step S107, the reliability determination unit 185 may calculate statistics of a plurality of measurement reliabilities corresponding to the plurality of second parallax images. For example, the statistics are a standard deviation or a histogram. The display control unit 181 may display the calculated statistics on the display unit 5.

Second Modified Example of First Embodiment

In the aforementioned example, measurement designation points are determined by adjusting the coordinates of the temporary designation points in step S109 after the temporary designation points are designated by the user in step S104. That is, a procedure for determining the measurement designation points is composed of two stages. However, the process in step S109 may be omitted if the coordinates of the temporary designation points are detected with accuracy which does not generate a problem in execution of measurement in step S104. The user may determine whether the process in step S109 is omitted.

Third Modified Example of First Embodiment

In the aforementioned example, the temporary designation points set in step S104 are used in the subsequent process. However, it may be assumed that a position that the user wants to measure is changed on the way. In this case, the user may change the temporary designation points set in step S104 while viewing the image displayed on the display unit 5 in step S112. For example, the user may change the positions, that is, the coordinates, of the temporary designation points to coordinates different from the initially set coordinates. Alternatively, the user may increase or decrease the number of temporary designation points. In the third modified example of the first embodiment, a step of updating information on a temporary designation point that may be changed by the user into latest information is added.

Figure 11:
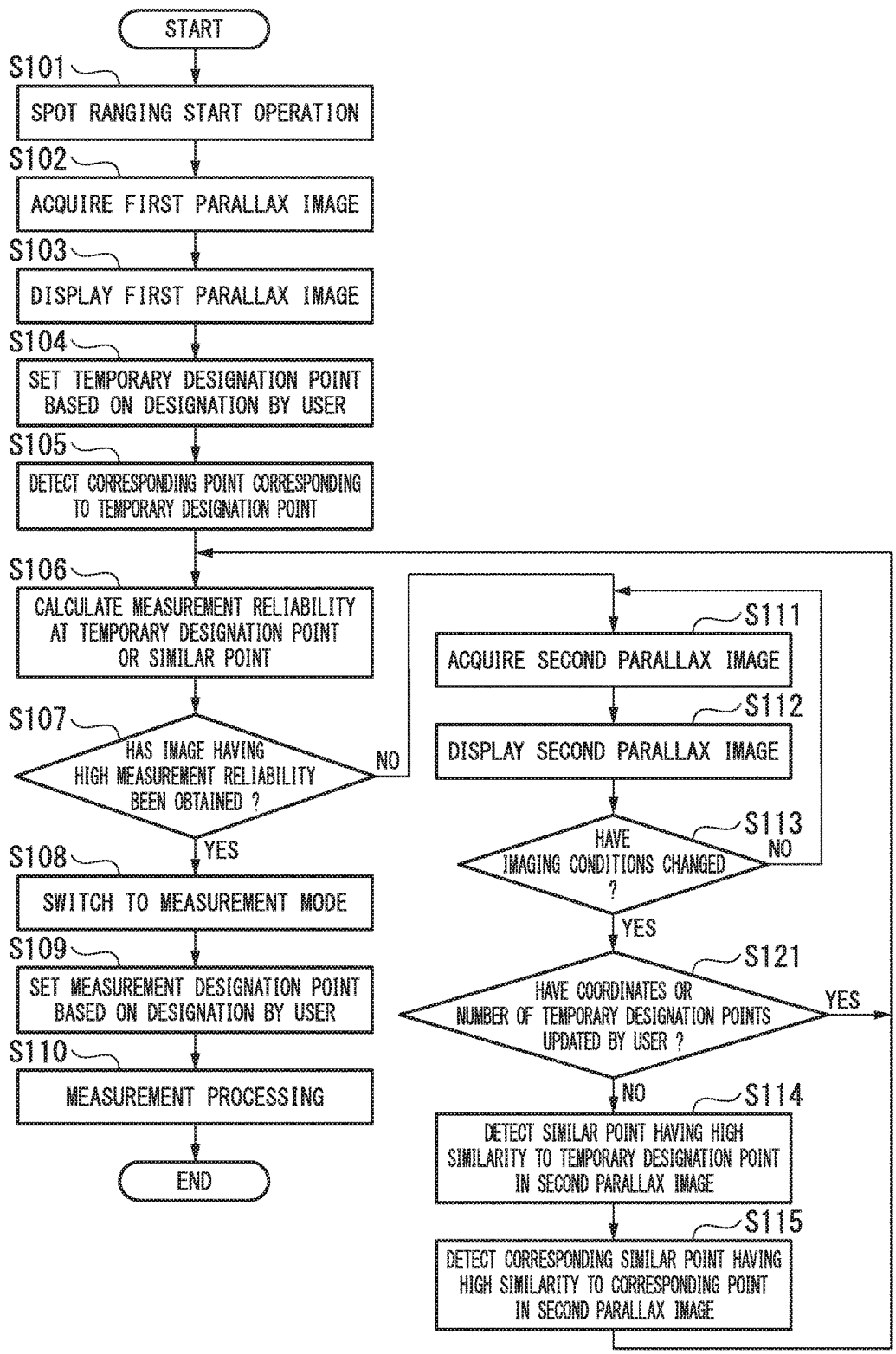
FIG. 11 is a flowchart showing a procedure of processes for measurement in a third modified example of the first embodiment of the present invention.

Processes in the third modified example of the first embodiment will be described using FIG. 11. FIG. 11 shows processes for measurement. In the processes shown in FIG. 11, differences from the processes shown in FIG. 7 will be described.

The temporary designation points are displayed at the same coordinates as the coordinates of the temporary designation points on the first parallax image when the second parallax image is displayed in step S112. The user may change the coordinates of the temporary designation points by operating the operation unit 4. The user may designate a new temporary designation point by operating the operation unit 4 to add the temporary designation point. The user may instruct a previously set temporary designation point to be cancelled by operating the operation unit 4 to cancel the temporary designation point.

When the imaging condition determination unit 186 determines that the imaging conditions have changed in step S113, the point detection unit 183 determines whether the coordinates or number of temporary designation points has changed by the user (step S121).

When the point detection unit 183 determines that the coordinates or number of temporary designation points has changed by the user in step S121, the process in step S106 is executed. In this case, coordinate information on the similar points is not present in step S106. Accordingly, measurement reliabilities at the designation points are calculated in step S106. When the user adds temporary designation points and thus a plurality of temporary designation points are present, a measurement reliability at each temporary designation point is calculated in step S106. When it is determined that measurement reliabilities of all temporary designation points are high in step S107, the process in step S108 is executed.

When the point detection unit 183 determines that the coordinates or number of temporary designation points has not changed by the user in step S121, the process in step S114 is executed.

A timing at which the process in step S121 is executed is not limited to the timing shown in FIG. 11. The process in step S121 may be executed at any timing within a period in which the processes from step S105 to step S114 are executed as long as coordinate information and the number of temporary designation points are updated to latest states. The timing at which the process in step S121 is executed is not included in a period in which the processes from step S108 to step S110 are executed.

With respect to points other than the above description, the processes shown in FIG. 11 are the same as the processes shown in FIG. 7.

Fourth Modified Example of First Embodiment

As described in the first embodiment, the second parallax image is acquired in step S111 and the imaging conditions are determined through comparison between the first parallax image and the second parallax image in step S113. However, the second parallax image is not necessarily acquired in determination of whether the imaging conditions have changed. For example, it may be determined whether the position or the posture of an endoscope has changed on the basis of information acquired by a small sensor incorporated in the tip 20 of the insertion part 2. The imaging condition determination unit 186 in the fourth modified example of the first embodiment determines whether at least one of the position and the posture of the imaging device 28 has changed. After the reliability determination unit 185 determines that the measurement reliability is low and the imaging condition determination unit 186 determines that the imaging conditions have changed, the imaging device 28 captures an image of the object which is the measurement target at the second timing and generates the second parallax image.

Figure 12:
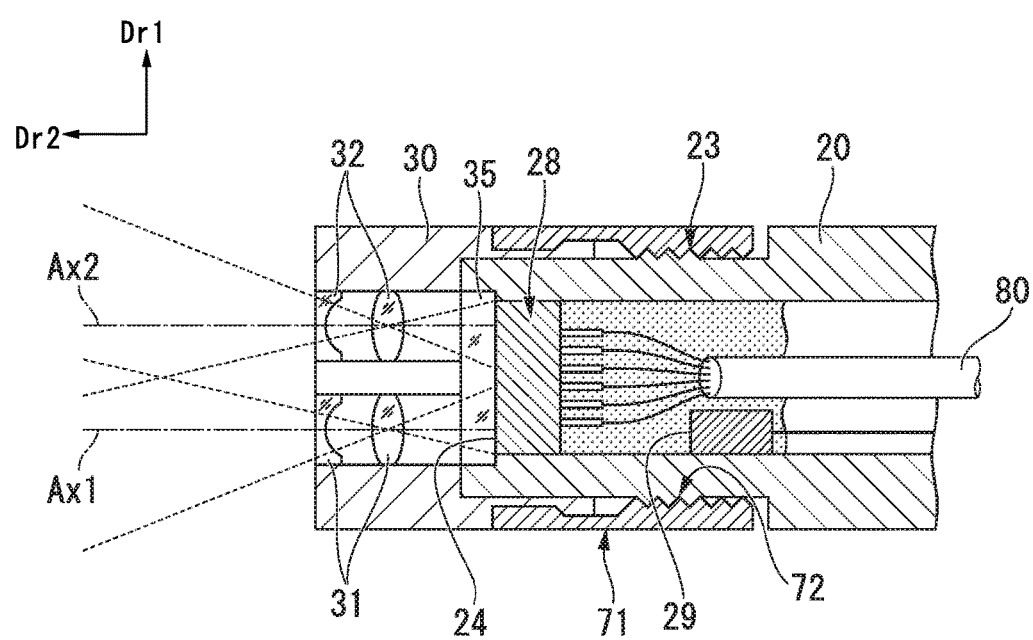
FIG. 12 is a cross-sectional view showing configurations of the tip of an insertion part and a stereo optical adapter in an endoscope apparatus according to a fourth modified example of the first embodiment of the present invention.

In the fourth modified example of the first embodiment, the configuration of the tip 20 of the insertion part 2 shown in FIG. 4 changes to a configuration shown in FIG. 12. FIG. 12 shows a cross section of the tip 20 of the insertion part 2 and the stereo optical adapter 30. With respect to the configuration shown in FIG. 12, differences from the configuration shown in FIG. 4 will be described.

As shown in FIG. 12, a sensor 29 is provided at the tip 20 of the insertion part 2. The sensor 29 is provided in proximity to the imaging device 28. The sensor 29 is separate from the imaging device 28. The sensor 29 may contact the imaging device 28. The sensor 29 may be provided inside of the imaging device 28. The sensor 29 is a magnetic sensor, an acceleration sensor, a gyro sensor or the like. The sensor 29 may detect at least one of the position and the posture of the imaging device 28 irrespective of a detection method set in the sensor 29. The sensor 29 outputs a signal indicating at least one of the position and the posture of the imaging device 28.

Figure 13:
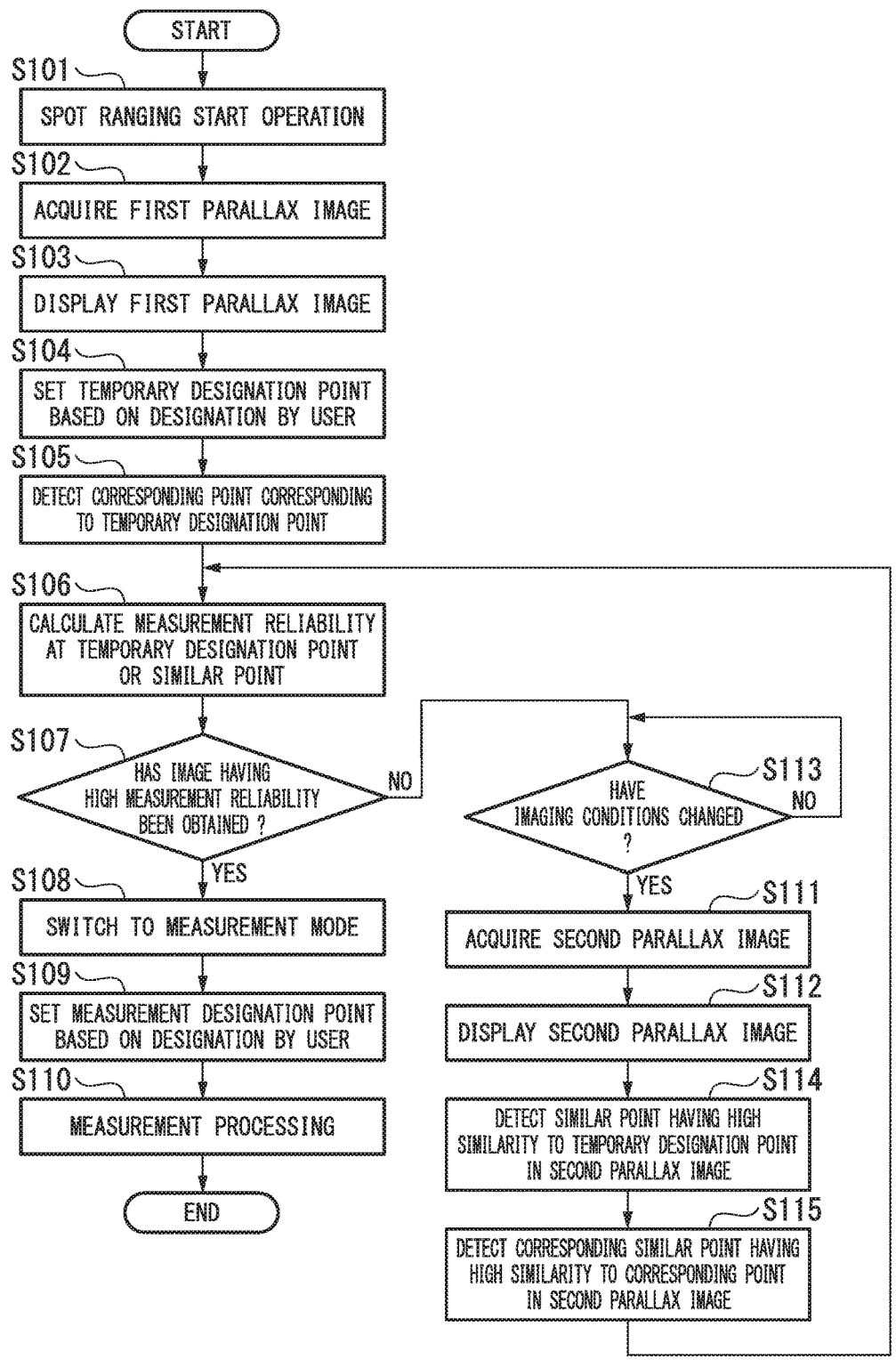
FIG. 13 is a flowchart showing a procedure of processes for measurement in the fourth modified example of the first embodiment of the present invention.

Processes in the fourth modified example of the first embodiment will be described using FIG. 13. FIG. 13 shows a procedure of processes for measurement. With respect to the processes shown in FIG. 13, differences from the processes shown in FIG. 7 will be described.

When the reliability determination unit 185 determines that the measurement reliability is low in step S107, the process in step S113 is executed. The imaging condition determination unit 186 determines whether a variation in the position or the posture of the imaging device 28, which is represented by the signal output from the sensor 29, is greater than a predetermined value set in advance in step S113. When the variation in the position or the posture of the imaging device 28 is greater than the predetermined value, the imaging condition determination unit 186 determines that the imaging conditions have changed. When the variation in the position or the posture of the imaging device 28 is smaller than the predetermined value, the imaging condition determination unit 186 determines that the imaging conditions have not changed.

When the imaging condition determination unit 186 determines that the imaging conditions have not changed in step S113, the process in step S113 is executed again. That is, determination of whether the imaging conditions have changed is repeated when the imaging condition have not changed. When the imaging condition determination unit 186 determines that the imaging conditions have changed in step S113, the process in step S111 is executed. After step S112, the process in step S114 is executed.

With respect to points other than the above description, the processes shown in FIG. 13 are the same as the processes shown in FIG. 7.

The imaging condition determination unit 186 may determine whether the imaging conditions have changed by determining whether the luminance of illumination has changed by the user. Alternatively, the imaging condition determination unit 186 may determine whether the imaging conditions have changed by determining whether a setting value of image processing (image processing parameter) has changed by the user. When the imaging condition determination unit 186 determines that the luminance of illumination has not changed by the user or the setting value of image processing has not changed in step S113, the process in step S113 is executed again. When the imaging condition determination unit 186 determines that the luminance of illumination has changed by the user or the setting value of image processing has changed in step S113, the process in step S111 is executed.

Second Embodiment

The endoscope apparatus 1 according to a second embodiment of the present invention has a function of supporting a user. Specifically, the endoscope apparatus 1 notifies the user of support information necessary to acquire an image suitable for measurement. Accordingly, the endoscope apparatus 1 can rapidly acquire an image suitable for measurement. The support information is composed of the cause of a low measurement reliability and a countermeasure for increasing the measurement reliability. The support information includes information for encouraging the user to perform at least one of change of the imaging conditions, change of designation points, and optimization of a mounting state of the stereo optical adapter 30 as a countermeasure for increasing the measurement reliability.

Figure 14:
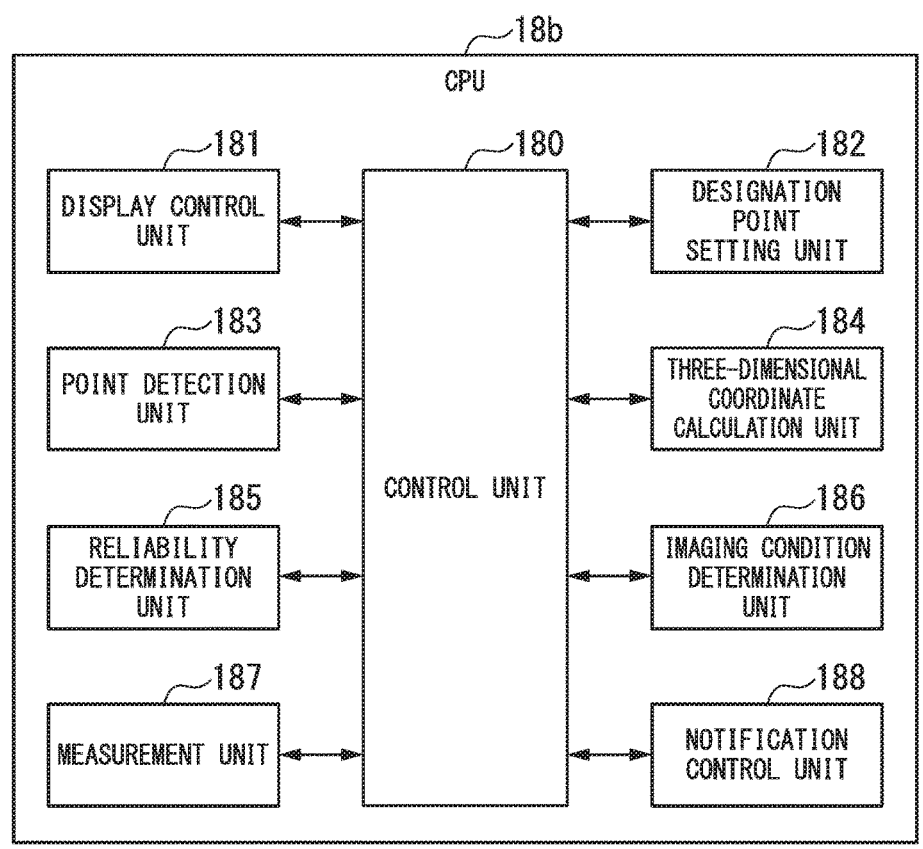
FIG. 14 is a block diagram showing a functional configuration of a CPU according to a second embodiment of the present invention.

In the second embodiment, the CPU 18a in the first embodiment is changed to a CPU 18b shown in FIG. 14. FIG. 14 shows a functional configuration of the CPU 18b. With respect to the configuration shown in FIG. 14, differences from the configuration shown in FIG. 5 will be described.

The CPU 18b has a notification control unit 188 in addition to the components shown in FIG. 5. After the reliability determination unit 185 determines that the measurement reliability is low and before the second parallax image is acquired, the notification control unit 188 notifies the user of information for increasing the measurement reliability. For example, the notification control unit 188 notifies the user of information for encouraging the user to change at last one of the position and the posture of the imaging device 28. Accordingly, the notification control unit 188 notifies the user of information for encouraging the user to change the imaging conditions of the imaging device 28 to conditions different from the imaging conditions at the first timing. The notification control unit 188 notifies the user of information for encouraging the user to change at least one of the position and the posture of the imaging device 28 such that the object distance changes.

Specifically, the notification control unit 188 displays a message or the like for increasing the measurement reliability on an image. For example, the notification control unit 188 generates a graphic image signal such as a message. The notification control unit 188 outputs the generated graphic image signal to the video signal processing circuit 12. The video signal processing circuit 12 combines a video signal output from the CCU 9 and the graphic image signal output from the CPU 18b. Accordingly, the message or the like is superimposed on the image. The video signal processing circuit 12 outputs the combined video signal to the display unit 5. The display unit 5 displays the image on which the message or the like is superimposed. The message or the like represents the cause of a low measurement reliability and a countermeasure for increasing the measurement reliability.

The method of notifying the user is not limited to display of information through the display unit 5. For example, a voice indicating information for increasing the measurement reliability may be output.

With respect to points other than the above description, the configuration shown in FIG. 14 is the same as the configuration shown in FIG. 5.

Figure 15:
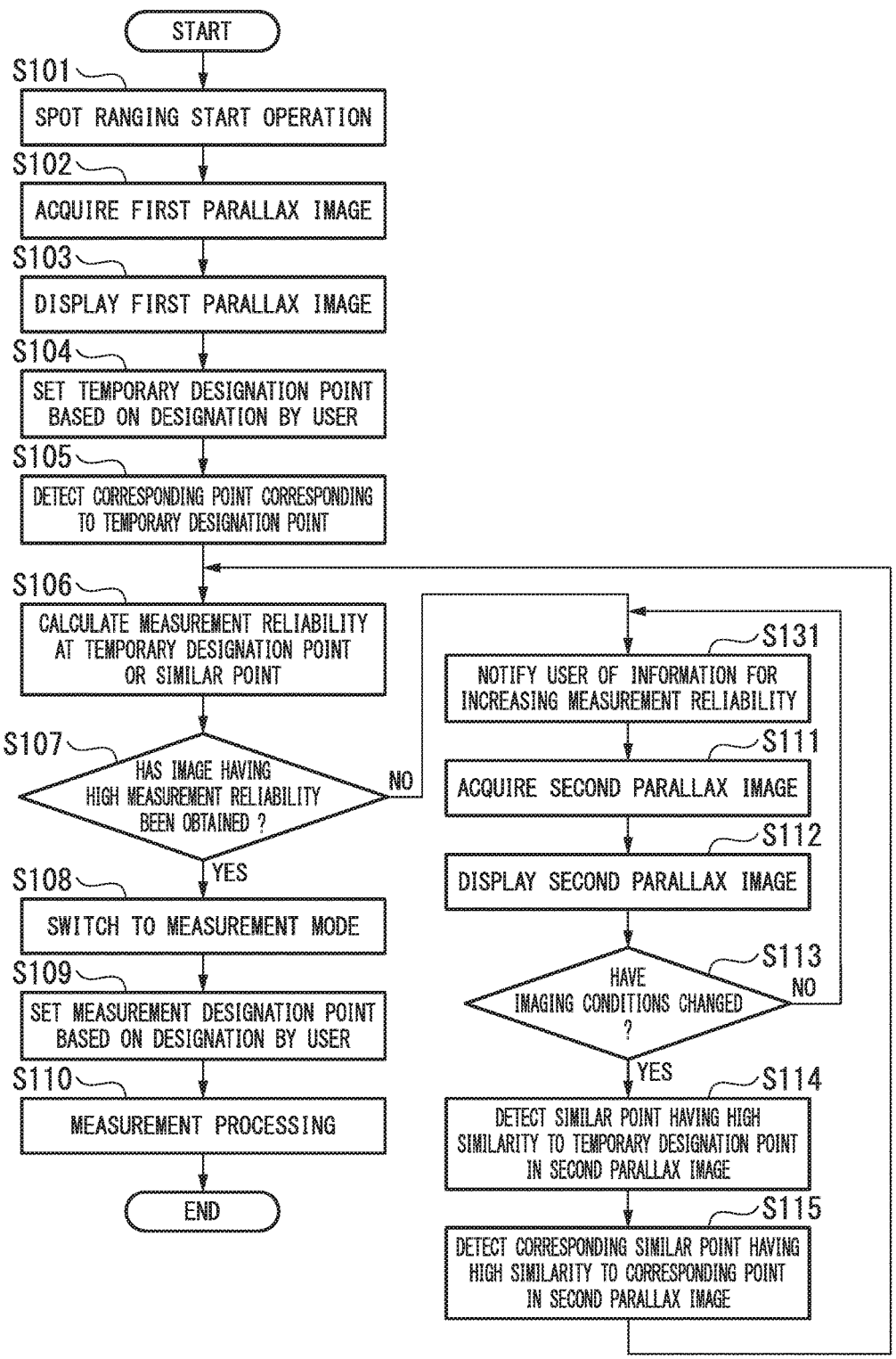
FIG. 15 is a flowchart showing a procedure of processes for measurement in the second embodiment of the present invention.

Processes in the second embodiment will be described using FIG. 15. FIG. 15 shows a procedure of processes for measurement. With respect to processes shown in FIG. 15, differences from the processes shown in FIG. 7 will be described.

When the reliability determination unit 185 determines that the measurement reliability is low in step S107, the notification control unit 188 notifies the user of information for increasing the measurement reliability (step S131). After step S131, the process in step S111 is executed. When the imaging condition determination unit 186 determines that the imaging conditions have not changed in step S113, the process in step S131 is executed.

With respect to points other than the above description, the processes shown in FIG. 15 are the same as the processes shown in FIG. 7.

Figure 16:
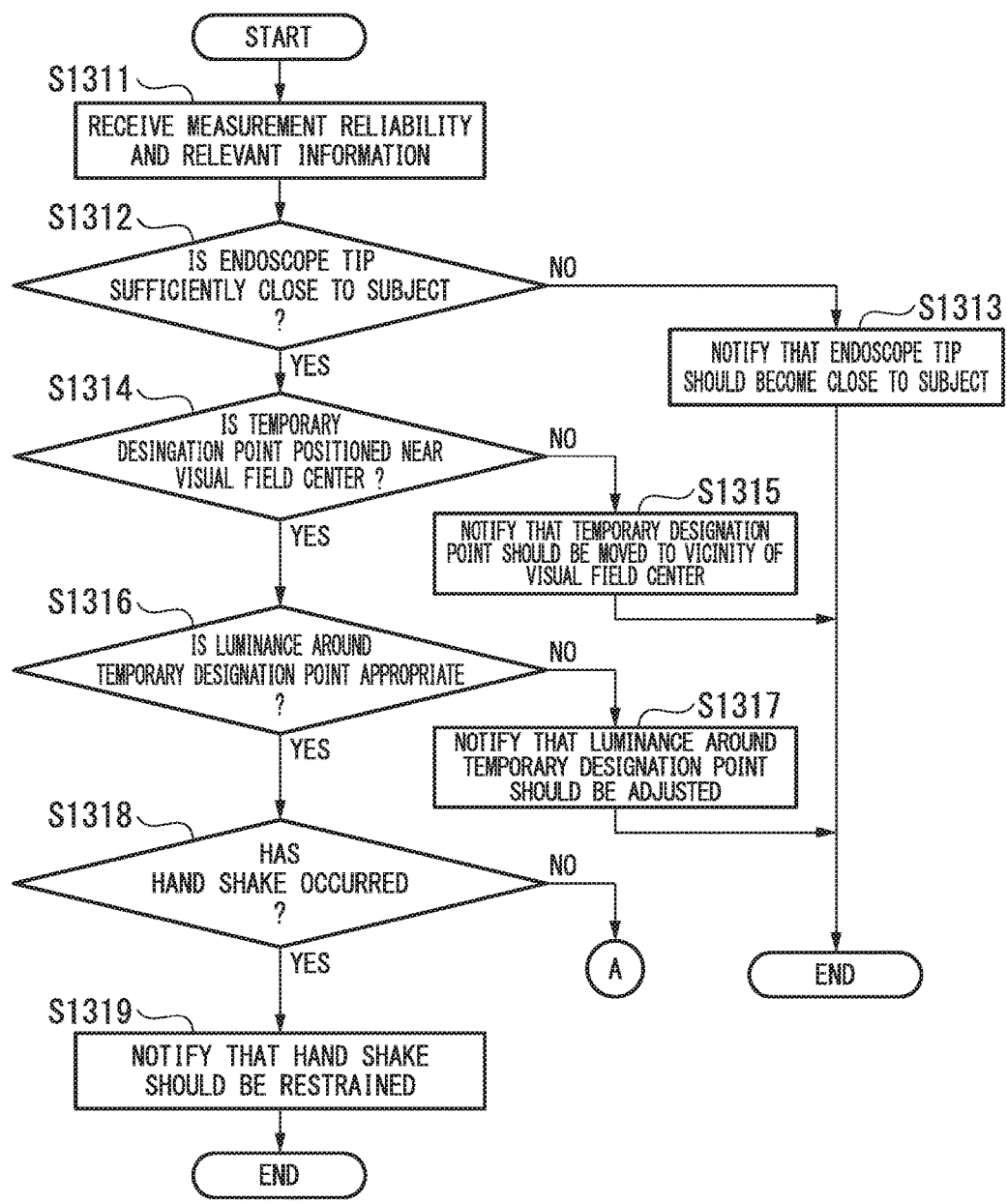
FIG. 16 is a flowchart showing a procedure of an information notification process for a user in the second embodiment of the present invention.
Figure 17:
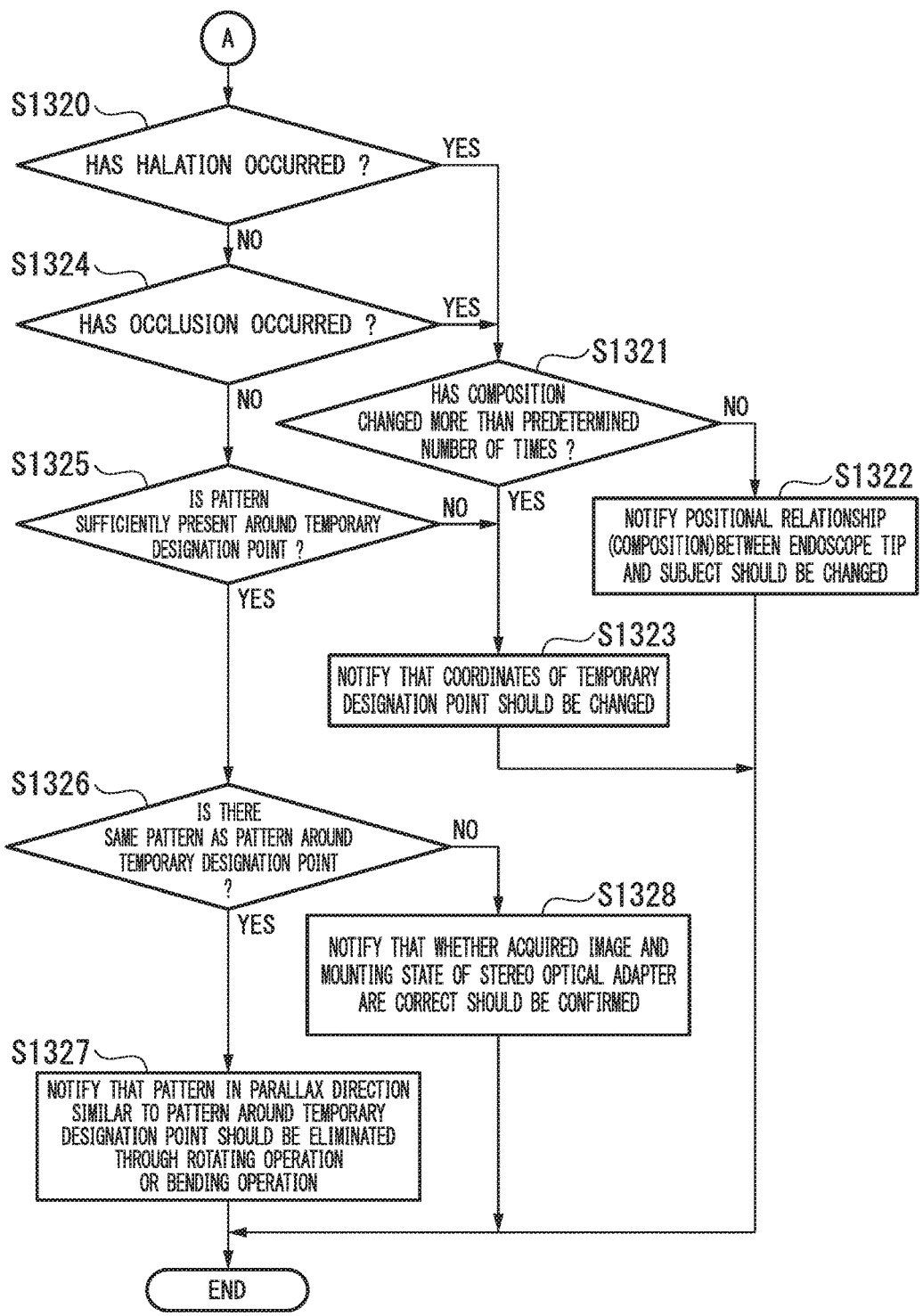
FIG. 17 is a flowchart showing the procedure of the information notification process for the user in the second embodiment of the present invention.

FIGS. 16 and 17 show a procedure of the process in step S131. An information notification process for the user will be described in detail using FIGS. 16 and 17.

The notification control unit 188 receives the measurement reliability output from the reliability determination unit 185 and relevant information thereof (step S1311). The relevant information is temporary designation point coordinates, two-dimensional images, three-dimensional coordinates and the like used for the reliability determination unit 185 to obtain the result.

After step S1311, the notification control unit 188 determines whether the object distance is sufficiently close using the z coordinate constituting the three-dimensional coordinates. Accordingly, the notification control unit 188 determines whether the endoscope tip (the tip 20 of the insertion part 2) is sufficiently close to the subject (step S1312).

When the notification control unit 188 determines that the object distance is not close in step S1312, the notification control unit 188 notifies the user that the user should bring the endoscope tip to close to the subject (step S1313). Accordingly, the notification control unit 188 notifies the user of information for encouraging the user to change the position of the imaging device 28. The processes shown in FIGS. 16 and 17 are ended by executing the process in step S1313.

Figure 18:
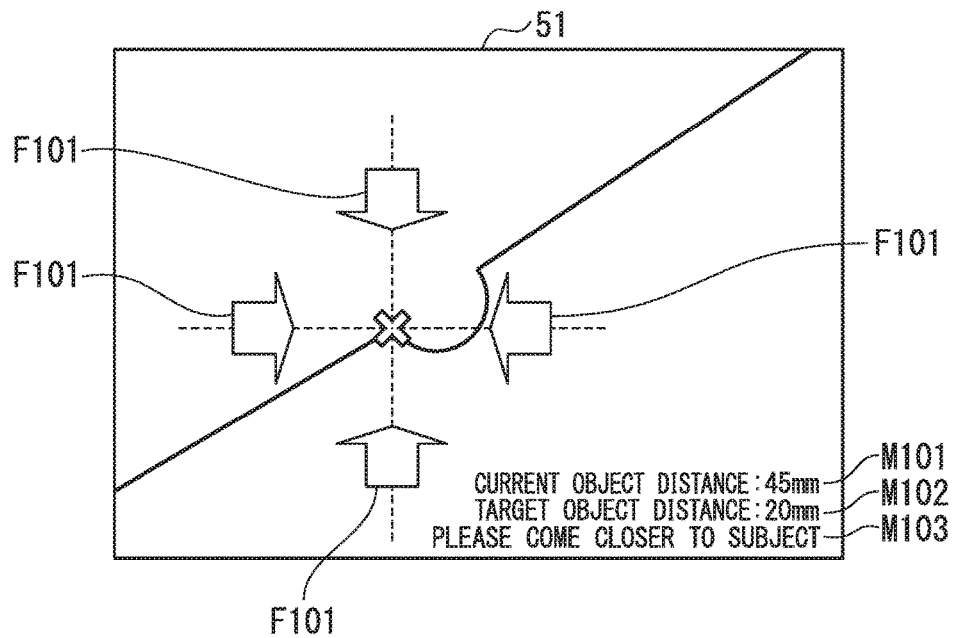
FIG. 18 is a diagram showing a display screen of a display unit in the second embodiment of the present invention.

FIG. 18 shows a display screen 51 of the display unit 5 in step S1313. As shown in FIG. 18, a current object distance M101, a target object distance M102 and a countermeasure M103 for realizing imaging conditions suitable for measurement are displayed on the display screen 51. In addition, a figure F101 for notifying the user that the user should bring the endoscope tip to close to the subject is displayed on the display screen 51. An icon or the like for notifying the user that the user should bring the endoscope tip to close to the subject may be displayed on the display screen 51.

When the notification control unit 188 determines that the object distance is sufficiently close in step S1312, the notification control unit 188 determines whether a temporary designation point designated by the user is near the visual field center (step S1314).

When the notification control unit 188 determines that the temporary designation point is not near the visual field center in step S1314, the notification control unit 188 notifies the user that the user should move the temporary designation point to the vicinity of the visual field center by a bending operation for changing the posture of the endoscope tip (step S1315). Accordingly, the notification control unit 188 notifies the user of information for encouraging the user to change the posture of the imaging device 28. The processes shown in FIGS. 16 and 17 are ended by executing the process in step S1315.

Figure 19:
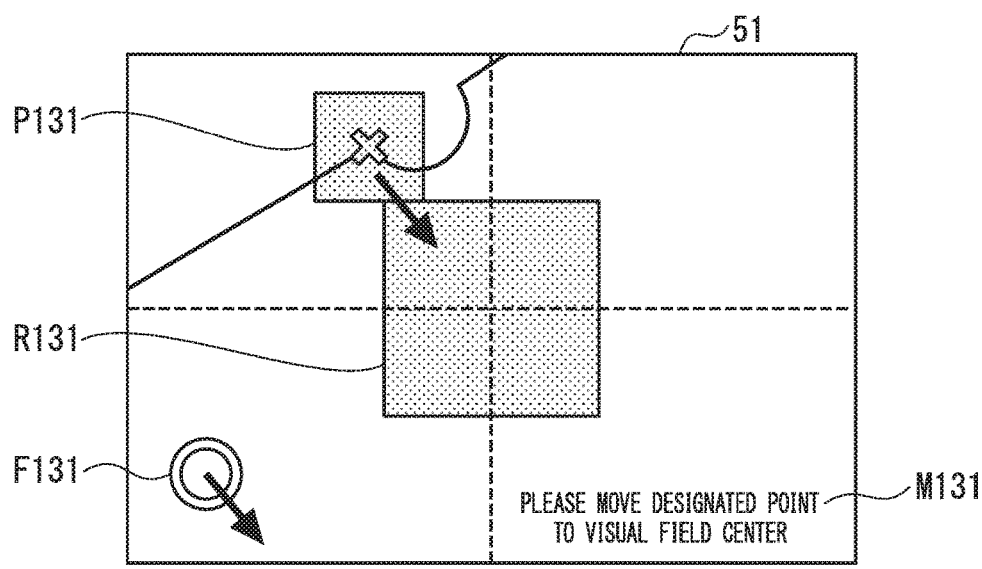
FIG. 19 is a diagram showing a display screen of the display unit in the second embodiment of the present invention.

FIG. 19 shows the display screen 51 of the display unit 5 in step S1315. As shown in FIG. 19, a current position P131 near the coordinates of the temporary designation point, a region R131 of the center of a target visual field and a countermeasure M131 for realizing imaging conditions suitable for measurement are displayed on the display screen 51. In addition, a figure F131 for notifying the user of an image of the bending operation is displayed on the display screen 51. An icon or the like for notifying the user of the image of the bending operation may be displayed on the display screen 51.

When the notification control unit 188 determines that the temporary designation point is near the visual field center in step S1314, the notification control unit 188 determines whether the luminance (brightness) of an image around the temporary designation point is appropriate (step S1316).

When the notification control unit 188 determines that the luminance of the image around the temporary designation point is not appropriate in step S1316, the notification control unit 188 notifies the user that the user should adjust luminance around the temporary designation point by increasing or decreasing the luminance value of the image (step S1317). The processes shown in FIGS. 16 and 17 are ended by executing the process in step S1317.

Figure 20:
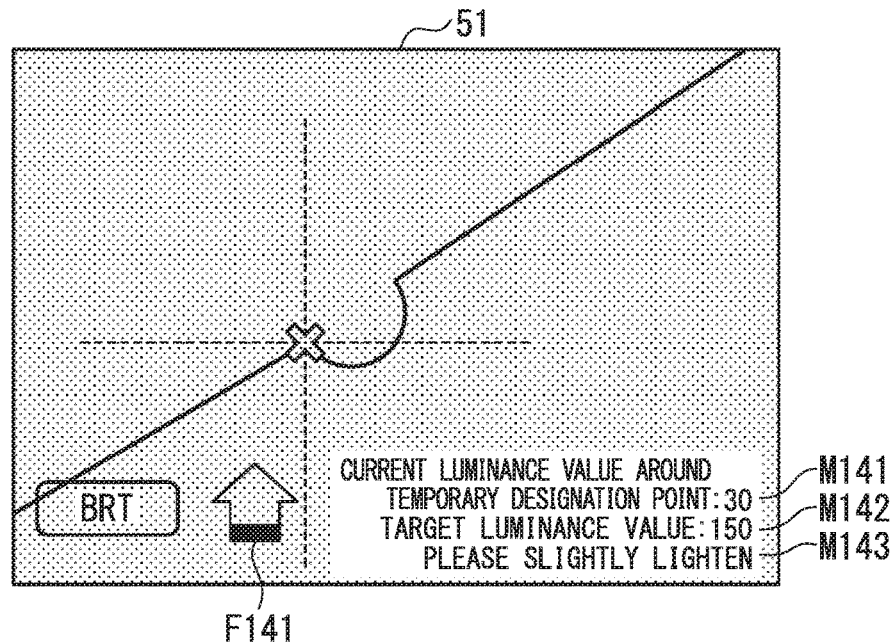
FIG. 20 is a diagram showing a display screen of the display unit in the second embodiment of the present invention.

FIG. 20 shows the display screen 51 of the display unit 5 in step S1317. As shown in FIG. 20, a current luminance value M141 around the coordinates of the temporary designation point, a target luminance value M142 and a countermeasure M143 for realizing imaging conditions suitable for measurement are displayed on the display screen 51. In addition, a figure F141 for notifying the user of an outline of luminance change is displayed on the display screen 51. An icon or the like for notifying the user of the outline of luminance change may be displayed on the display screen 51.

When the notification control unit 188 determines that the luminance of the image around the temporary designation point is appropriate in step S1316, the notification control unit 188 determines whether hand shake has occurred (step S1318). For example, the notification control unit 188 determines whether hand shake has occurred by comparing continuously acquired two pairs of parallax images in step S1318. When the endoscope apparatus 1 has the sensor 29 shown in FIG. 12, the notification control unit 188 may determine whether hand shake has occurred on the basis of a signal output from the sensor 29.

When the notification control unit 188 determines that hand shake has occurred in step S1318, the notification control unit 188 notifies the user that the user should restrain the hand shake at the endoscope tip (step S1319). The processes shown in FIGS. 16 and 17 are ended by executing the process in step S1319.

Figure 21:
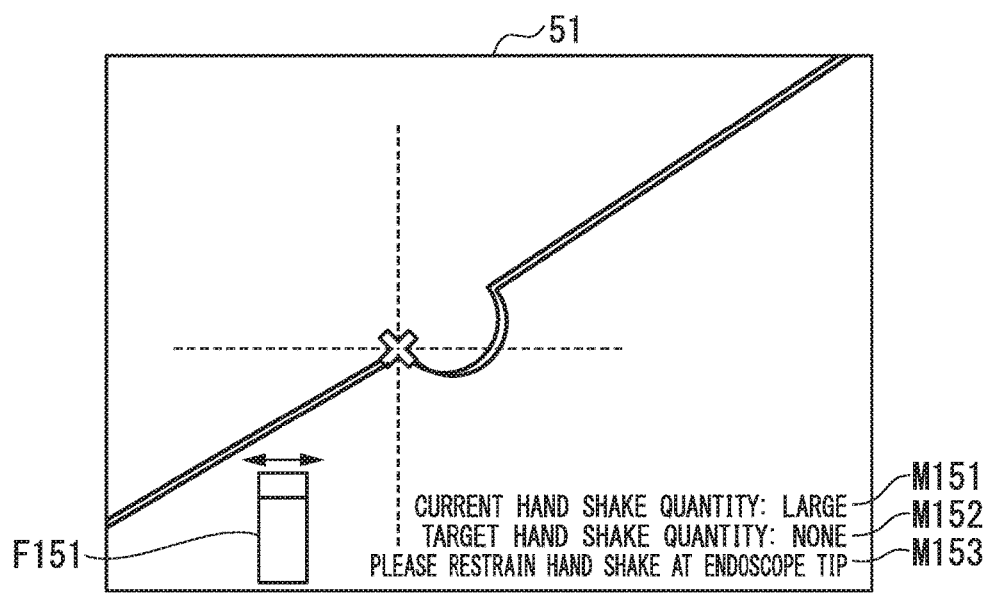
FIG. 21 is a diagram showing a display screen of the display unit in the second embodiment of the present invention.

FIG. 21 shows the display screen 51 of the display unit 5 in step S1319. As shown in FIG. 21, a current hand shake quantity M151, a target hand shake quantity M152 and a countermeasure M153 for realizing imaging conditions suitable for measurement are displayed on the display screen 51. In addition, a figure F151 for notifying the user of an image for restraining hand shake at the endoscope tip is displayed on the display screen 51. An icon or the like for notifying the user of the image for restraining hand shake at the endoscope tip may be displayed on the display screen 51.

When the notification control unit 188 determines that hand shake has not occurred in step S1318, the notification control unit 188 determines whether halation has occurred around the temporary designation point (step S1320).

When the notification control unit 188 determines that halation has occurred in step S1320, the notification control unit 188 determines whether the composition has changed more than a predetermined number of times (step S1321).

When the notification control unit 188 determines that the composition has changed only the predetermined number of times or less in step S1321, the notification control unit 188 notifies the user that the user should change the positional relationship between the endoscope tip and the subject, that is, the composition, such that the region around the temporary designation point does not overlap with the halation (step S1322). Accordingly, the notification control unit 188 notifies the user of information for encouraging the user to change at least one of the position and the posture of the imaging device 28. The processes shown in FIGS. 16 and 17 are ended by executing the process in step S1322.

When the notification control unit 188 determines that the composition has changed more than the predetermined number of times in step S1321, the notification control unit 188 determines that halation that has occurred around the temporary designation point cannot be avoided even when the composition is changed. Accordingly, the notification control unit 188 notifies the user that the user should change the coordinates of the temporary designation point (step S1323). Accordingly, the notification control unit 188 notifies the user of information for encouraging the user to change the temporary designation point. The processes shown in FIGS. 16 and 17 are ended by executing the process in step S1323. The upper limit and the lower limit of the predetermined number of times which is a criterion for determination in step S1321 are not limited.

When the notification control unit 188 determines that halation has not occurred in step S1320, the notification control unit 188 determines whether occlusion has occurred (step S1324). The occlusion is a state in which a region which can be viewed in an optical image obtained by one of the first optical system 31 and the second optical system 32 and cannot be viewed in an optical image obtained by the other one of the first optical system 31 and the second optical system 32 is generated.

When the notification control unit 188 determines that occlusion has occurred in step S1324, the process in step S1321 is executed. When the notification control unit 188 determines that occlusion has not occurred in step S1324, the notification control unit 188 determines whether the pattern of the subject is sufficiently present near the temporary designation point (step S1325).

When the notification control unit 188 determines that the pattern of the subject is not sufficiently present near the temporary designation point in step S1325, the measurement accuracy decreases. Accordingly, the notification control unit 188 notifies the user that the user should change the temporary designation point to coordinates at which a sufficient pattern is present (step S1323). When the notification control unit 188 determines that the pattern of the subject is not present at all near the temporary designation point in step S1325, the process in step S1323 is executed.

When the notification control unit 188 determines that the pattern of the subject is sufficiently present near the temporary designation point in step S1325, the notification control unit 188 determines whether the same pattern as the pattern near the temporary designation point is present at coordinates separated from the temporary designation point in the parallax direction (step S1326).

When the notification control unit 188 determines that the same pattern as the pattern near the temporary designation point is present at the coordinates separated from the temporary designation point in the parallax direction in step S1326, the measurement accuracy decreases. Accordingly, the notification control unit 188 notifies the user that the user should eliminate a pattern in the parallax direction which is similar to the pattern near the temporary designation point by performing a rotating operation or a bending operation around the optical axis of the endoscope tip (step S1327). Accordingly, the notification control unit 188 notifies the user of information for encouraging the user to change the posture of the imaging device 28. For example, the rotating operation around the optical axis of the endoscope tip is an operation of twisting the endoscope tip. The processes shown in FIGS. 16 and 17 are ended by executing the process in step S1327.

When the notification control unit 188 determines that the same pattern as the pattern near the temporary designation point is not present at the coordinates separated from the temporary designation point in the parallax direction in step S1326, the acquired image or the mounting state of the stereo optical adapter 30 may not be correct. Accordingly, the notification control unit 188 notifies the user that the user should check such a state (step S1328). Accordingly, the notification control unit 188 notifies the user of information for encouraging the user to optimize the mounting state of the stereo optical adapter 30. The processes shown in FIGS. 16 and 17 are ended by executing the process in step S1328.

The notification control unit 188 notifies the user of information for encouraging the user to change the imaging conditions of the imaging device 28 to conditions different from the imaging conditions at the first timing through the processes in steps S1313, S1315, S1317, S1319, S1322 and S1327.

The three-dimensional coordinate calculation unit 184 calculates three-dimensional coordinates of the temporary designation point in step S106. The z coordinate constituting the calculated three-dimensional coordinates indicates the object distance. Accordingly, the three-dimensional coordinate calculation unit 184 (object distance measurement unit) measures the object distance in step S106. The notification control unit 188 notifies the user of information for increasing the measurement reliability in step S131 and the second parallax image is acquired in step S111. Thereafter, the imaging condition determination unit 186 determines whether the imaging conditions have changed by determining whether the object distance measured by the three-dimensional coordinate calculation unit 184 has changed.

A processing unit separate from the notification control unit 188 may execute processes with respect to determination among the processes shown in FIGS. 16 and 17 and the notification control unit 188 may execute only processes with respect to notification.

The processes shown in FIGS. 16 and 17 are an example. The order of respective steps may be changed. Some steps may be omitted. One step may be divided into a plurality of steps. For example, after it is confirmed that the endoscope tip is sufficiently close to the subject and the temporary designation point is present near the visual field center, it may be determined whether the endoscope tip is sufficiently close to the subject again.

In the second embodiment, the user is notified of the support information for realizing imaging conditions suitable for measurement. Accordingly, the endoscope apparatus 1 can rapidly acquire an image suitable for measurement compared to the first embodiment. Therefore, inspection efficiency is improved.

Third Embodiment

The endoscope apparatus 1 according to the third embodiment of the present invention automatically changes imaging conditions to conditions suitable for measurement. As in the first embodiment and the fourth modified example thereof, the imaging conditions include the brightness of illumination and a setting value of image processing (image processing parameter) in addition to the position and the posture of the imaging device 28.

Figure 22:
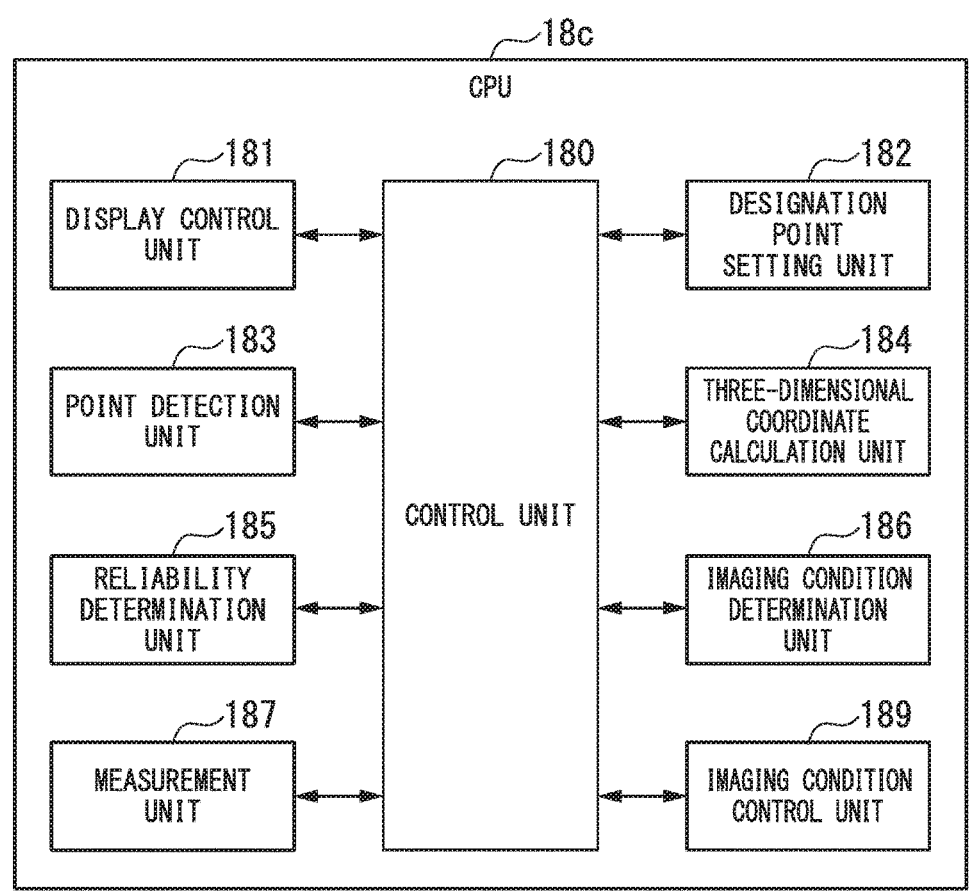
FIG. 22 is a block diagram showing a functional configuration of a CPU according to a third embodiment of the present invention.

In the third embodiment, the CPU 18*a* in the first embodiment is changed to a CPU 18*c* shown in FIG. 22. FIG. 22 shows a functional configuration of the CPU 18*c*. With respect to the configuration shown in FIG. 22, differences from the configuration shown in FIG. 5 will be described.

The CPU 18*c* has an imaging condition control unit 189 in addition to the components shown in FIG. 5. After the reliability determination unit 185 determines that the measurement reliability is low and before the second parallax image is acquired, the imaging condition control unit 189 changes the imaging conditions of the imaging device 28 such that the measurement reliability increases. The imaging condition control unit 189 changes the imaging conditions at the second timing to conditions different from the imaging conditions at the first timing such that the measurement reliability increases. Accordingly, the measurement reliability is improved compared to that before the imaging conditions are changed.

The imaging conditions are at least one of the position and the posture of the imaging device 28. The imaging conditions may be an object distance between an object and an optical system which causes light from the object which is a measurement target to enter the imaging device 28. The imaging conditions may be at least one of the brightness of illumination and a setting value of image processing.

With respect to points other than the above description, the components shown in FIG. 22 are the same as the components shown in FIG. 5.

Figure 23:
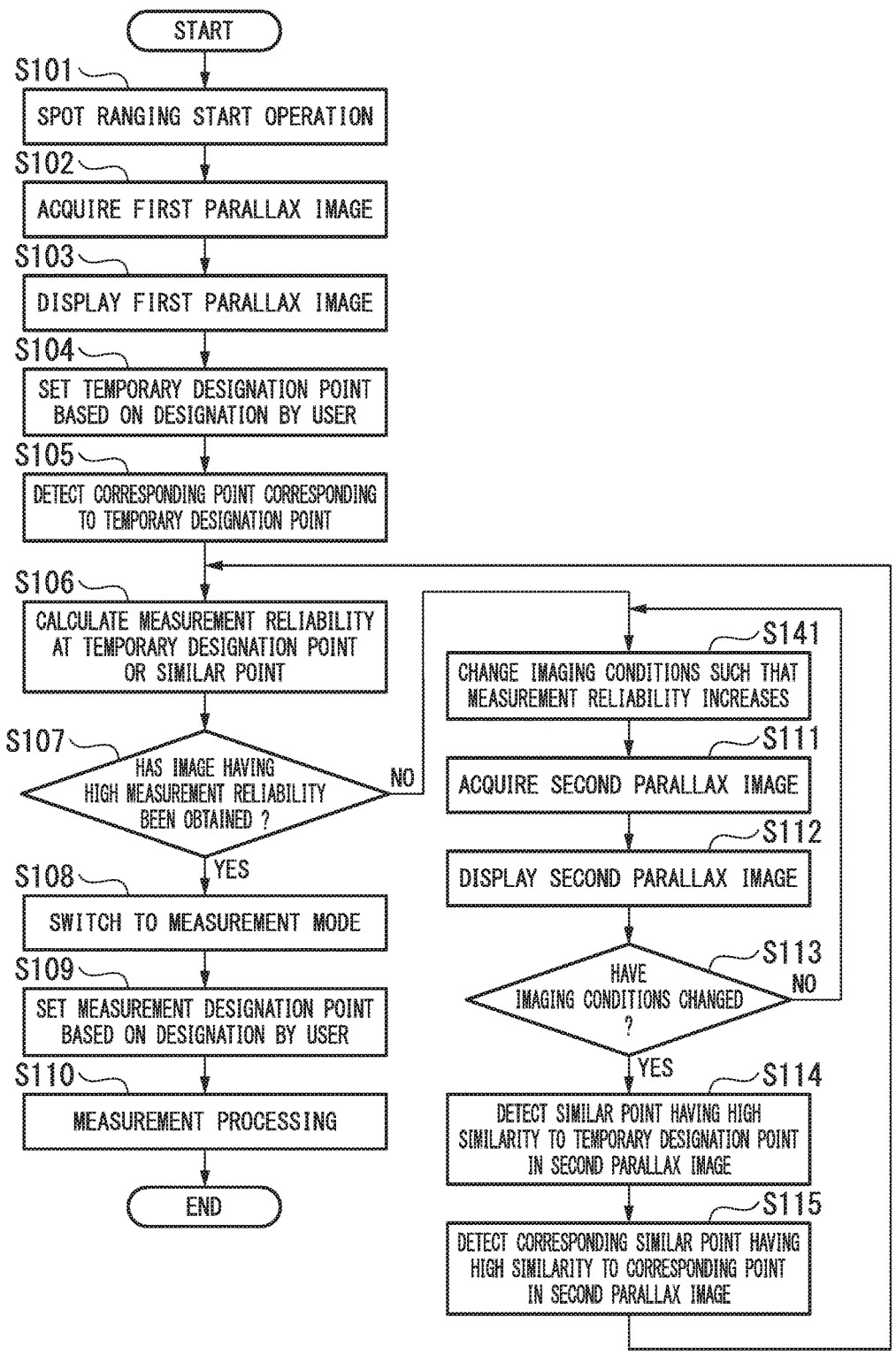
FIG. 23 is a flowchart showing a procedure of processes for measurement in the third embodiment of the present invention.

Processes in the third embodiment will be described using FIG. 23. FIG. 23 shows a procedure of processes for measurement. With respect to processes shown in FIG. 23, differences from the processes shown in FIG. 7 will be described.

When the reliability determination unit 185 determines that the measurement reliability is low in step S107, the imaging condition control unit 189 changes the imaging conditions of the imaging device 28 such that the measurement reliability increases (step S141). After step S141, the process in step S111 is executed. When the imaging condition determination unit 186 determines that the imaging conditions have not changed in step S113, the process in step S141 is executed.

With respect points other than the above description, the processes shown in FIG. 23 are the same as the processes shown in FIG. 7.

Figure 24:
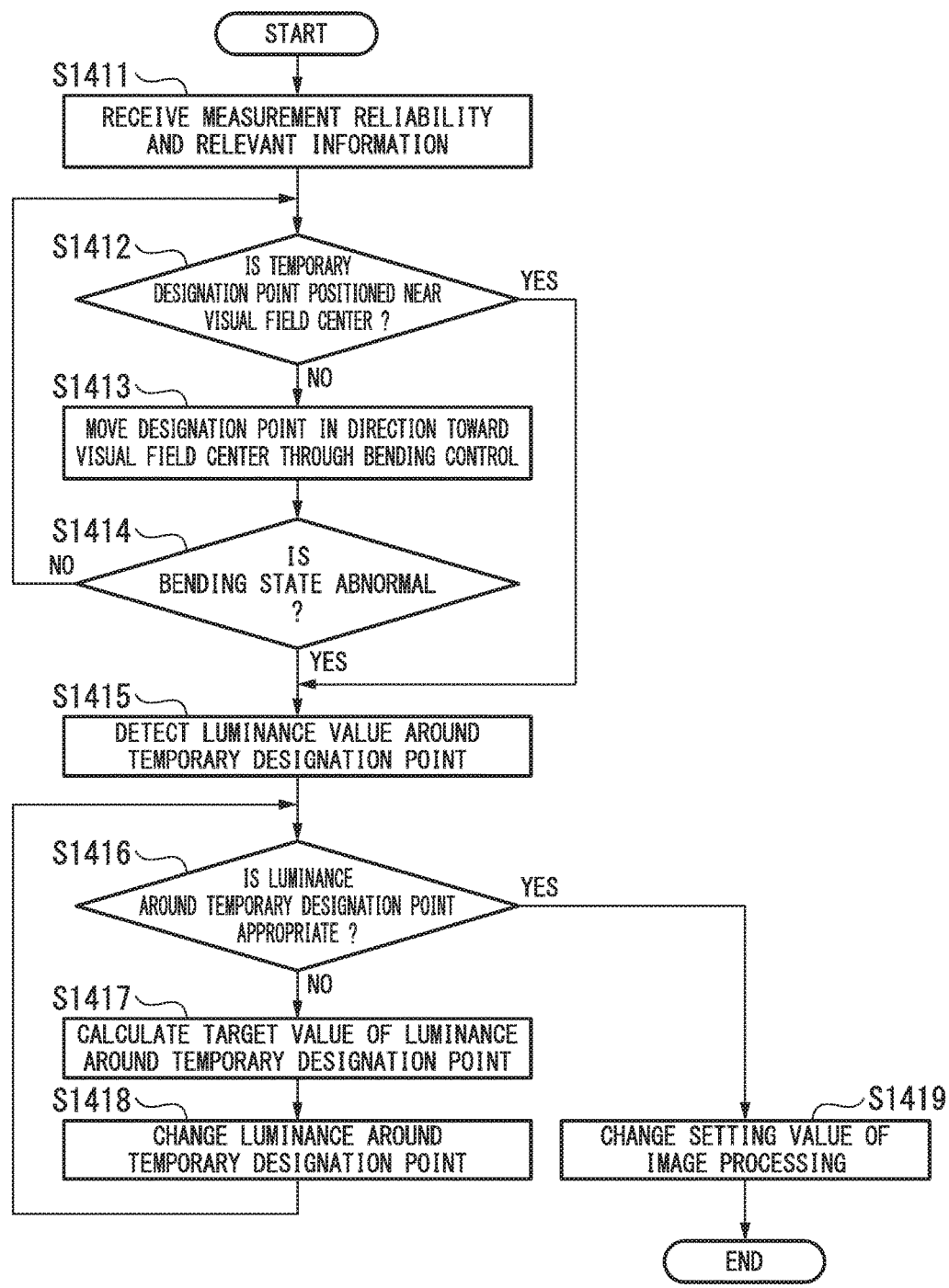
FIG. 24 is a flowchart showing a procedure of an imaging condition change process in the third embodiment of the present invention.

FIG. 24 shows a procedure of the process in step S141. The imaging condition change process will be described in detail using FIG. 24.

The imaging condition control unit 189 receives the measurement reliability output from the reliability determination unit 185 and relevant information thereof (step S1411). The relevant information is the temporary designation point coordinates, three-dimensional coordinates and the like used for the reliability determination unit 185 to obtain the result.

After step S1411, the imaging condition control unit 189 determines whether the temporary designation point designated by the user is near the visual field center (step S1412).

When the imaging condition control unit 189 determines that the temporary designation point is near the visual field center in step S1412, the process in step S1415 is executed. When the imaging condition control unit 189 determines that the temporary designation point is not near the visual field center in step S1412, the imaging condition control unit 189 moves the temporary designation point in the direction toward the visual field center through bending control for changing the posture of the endoscope tip (step S1413).

The imaging condition control unit 189 controls a bending mechanism for bending the tip 20 of the insertion part 2 in step S1413. For example, the imaging condition control unit 189 generates a command for bending the tip 20 of the insertion part 2 in any one of upward, downward, left and right directions. The command generated by the imaging condition control unit 189 is output to the endoscope unit 8 through the control interface 17. The endoscope unit 8 bends the tip 20 of the insertion part 2 by driving the bending mechanism on the basis of the command.

After step S1413, the imaging condition control unit 189 determines whether a bending state is abnormal (step S1414). For example, an abnormal bending state is a state in which a bending angle has already reached the limit even when the imaging condition control unit 189 attempts to move the temporary designation point to the visual field center. Otherwise, an abnormal bending state is a state in which the endoscope tip is caught in a part of a subject and thus bending does not work, or the like.

When the imaging condition control unit 189 determines that the bending state is not abnormal in step S1414, the process in step S1412 is executed. When the imaging condition control unit 189 determines that the bending state is abnormal in step S1414, the imaging condition control unit 189 stops the bending operation. Thereafter, a process in step S1415 is executed.

The imaging condition control unit 189 detects the luminance (brightness) of the image around the temporary designation point (step S1415). After step S1415, the imaging condition control unit 189 determines whether the luminance of the image around the temporary designation point is appropriate (step S1416).

When the imaging condition control unit 189 determines that the luminance of the image around the temporary designation point is not appropriate in step S1416, the imaging condition control unit 189 calculates a target value of the luminance of the image around the temporary designation point (step S1417). When the target value is set in advance, the imaging condition control unit 189 reads the target value from the RAM 14 in step S1417.

After step S1417, the imaging condition control unit 189 controls an exposure time, a gain and the quantity of light of a light source such that the luminance becomes close to the target value calculated in step S1417. Accordingly, the imaging condition control unit 189 changes the luminance of the image around the temporary designation point (step S1418). After step S1418, the process in step S1416 is executed.

When the imaging condition control unit 189 determines that the luminance of the image around the temporary designation point is appropriate in step S1416, the imaging condition control unit 189 determines that the setting value of image processing is inappropriate. Accordingly, the imaging condition control unit 189 changes the setting value of image processing (step S1419). The processes shown in FIG. 24 are ended by executing the process in step S1419.

The processes shown in FIG. 24 are an example. The order of the respective steps may be changed. Some steps may be omitted. One step may be divided into a plurality of steps. For example, the luminance around the temporary designation point is appropriately controlled after the temporary designation point is moved to the vicinity of the visual field center. Thereafter, if the temporary designation point is deviated from the vicinity of the visual field center, the process of moving the temporary designation point to the vicinity of the visual field center may be executed again.

The endoscope apparatus 1 may change only some of imaging conditions, which can be changed. The process of notifying the user of the support information in the second embodiment may be executed after step S141.

In the third embodiment, the user need not purposely change various imaging conditions. The endoscope apparatus 1 automatically changes imaging conditions, and thus a user having a low degree of skill can also easily acquire an image suitable for measurement. Accordingly, inspection efficiency is improved.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A measurement apparatus comprising:
   an imaging unit configured to capture an image of an object which is a measurement target and generate a parallax image including two images having a parallax therebetween;
   a display control unit configured to cause a display unit to display at least one of the two images, the two images displayed on the display unit being included in a first parallax image which is the parallax image generated when an image of the object is captured at a first timing;
   a designation point setting unit configured to set a designation point in an image which is one of the two images included in the first parallax image and is displayed on the display unit;
   a point detection unit configured to detect a corresponding point corresponding to the designation point in an image which is the other of the two images included in the first parallax image and differs from the image in which the designation point has been set;
   a reliability determination unit configured to determine a measurement reliability on the basis of the designation point and the corresponding point;
   a measurement unit configured to perform measurement of the object using the parallax image when the reliability determination unit determines that the measurement reliability is high; and
   an imaging condition determination unit configured to determine whether imaging conditions of the imaging unit have changed from imaging conditions at the first timing after the reliability determination unit determines that the measurement reliability is low,
   wherein, the imaging unit is configured to capture an image of the object at a second timing and generate a second parallax image which is the parallax image including the two images after the reliability determination unit determines that the measurement reliability is low,
   the point detection unit is configured to detect a similar point in one of the two images included in the second parallax image after the imaging condition determination unit determines that the imaging conditions have changed, the similar point being similar to the designation point set in one of the two images included in the first parallax image,
   the point detection unit is configured to detect a similar corresponding point corresponding to the similar point in an image which is the other of the two images included in the second parallax image and differs from the image in which the similar point is detected, and
   the reliability determination unit is configured to determine the measurement reliability on the basis of the similar point and the similar corresponding point.

2. The measurement apparatus according to claim 1, wherein the imaging condition determination unit is configured to determine whether the imaging conditions of the imaging unit have changed from the imaging conditions at the first timing after the second parallax image is generated.

3. The measurement apparatus according to claim 1, wherein the imaging unit is configured to capture an image of the object at the second timing and generate the second parallax image after the reliability determination unit determines that the measurement reliability is low and the imaging condition determination unit determines that the imaging conditions have changed.

4. The measurement apparatus according to claim 1, further comprising a notification control unit configured to notify a user of information for increasing the measurement reliability after the reliability determination unit determines that the measurement reliability is low and before the second parallax image is acquired.

5. The measurement apparatus according to claim 4, wherein the notification control unit is configured to notify the user of the information for encouraging the user to change at least one of the position of the imaging unit and the posture of the imaging unit.

6. The measurement apparatus according to claim 5, wherein the notification control unit is configured to notify the user of the information for encouraging the user to change at least one of the position of the imaging unit and the posture of the imaging unit such that an object distance between an optical system and the object changes, the optical system causing light from the object to enter the imaging unit.

7. The measurement apparatus according to claim 6, further comprising an object distance measurement unit configured to measure the object distance,
   wherein the imaging condition determination unit is configured to determine whether the imaging conditions have changed by determining whether the object distance measured by the object distance measurement unit has changed after the notification control unit notifies the user of the information and the second parallax image is acquired.

8. The measurement apparatus according to claim 4, wherein the notification control unit is configured to notify the user of the information for encouraging the user to change the imaging conditions of the imaging unit to conditions different from the imaging conditions at the first timing.

9. The measurement apparatus according to claim 1, further comprising an imaging condition control unit configured to change the imaging conditions of the imaging unit such that the measurement reliability increases after the reliability determination unit determines that the measurement reliability is low and before the second parallax image is acquired.

10. The measurement apparatus according to claim 9, wherein the imaging conditions are at least one of the position of the imaging unit and the posture of the imaging unit.

11. The measurement apparatus according to claim 10, wherein the imaging conditions are an object distance between an optical system and the object, the optical system causing light from the object to enter the imaging unit.

12. The measurement apparatus according to claim 9, wherein the imaging condition control unit is configured to change the imaging conditions at the second timing to conditions different from the imaging conditions at the first timing.

13. An operation method of a measurement apparatus, comprising:
   a first imaging step in which the measurement apparatus captures an image of an object which is a measurement target at a first timing and generates a first parallax image including two images having a parallax therebetween by an imaging unit;
   a display step in which the measurement apparatus causes a display unit to display at least one of the two images included in the first parallax image;
   a designation point setting step in which the measurement apparatus sets a designation point in an image which is one of the two images included in the first parallax image and is displayed on the display unit;

a first point detection step in which the measurement apparatus detects a corresponding point corresponding to the designation point in an image which is the other of the two images included in the first parallax image and differs from the image in which the designation point has been set;

a first reliability determination step in which the measurement apparatus determines a measurement reliability on the basis of the designation point and the corresponding point;

a first measurement step in which the measurement apparatus performs measurement of the object using the first parallax image when the measurement reliability is determined to be high in the first reliability determination step;

an imaging condition determination step in which the measurement apparatus determines whether imaging conditions of the imaging unit have changed from imaging conditions at the first timing after the measurement reliability is determined to be low in the first reliability determination step;

a second imaging step in which the measurement apparatus captures an image of the object at a second timing and generates a second parallax image including the two images by the imaging unit after the measurement reliability is determined to be low in the first reliability determination step;

a second point detection step in which the measurement apparatus detects a similar point in one of the two images included in the second parallax image after it is determined that the imaging conditions have changed in the imaging condition determination step, the similar point being similar to the designation point set in one of the two images included in the first parallax image;

a third point detection step in which the measurement apparatus detects a similar corresponding point corresponding to the similar point in an image which is the other of the two images included in the second parallax image and differs from the image in which the similar point is detected;

a second reliability determination step in which the measurement apparatus determines the measurement reliability on the basis of the similar point and the similar corresponding point; and a second measurement step in which the measurement apparatus performs measurement of the object using the second parallax image when the measurement reliability is determined to be high in the second reliability determination step.

\* \* \* \* \*